(12) United States Patent
Xie et al.

(10) Patent No.: US 10,646,570 B2
(45) Date of Patent: May 12, 2020

(54) INDUCED PHOTODYNAMIC THERAPY USING NANOPARTICLE SCINTILLATORS AS TRANSDUCERS

(71) Applicant: UNIVERSITY OF GEORGIA RESEARCH FOUNDATION, INC., Athens, GA (US)

(72) Inventors: Jin Xie, Athens, GA (US); Hongmin Chen, Athens, GA (US); Geoffrey D. Wang, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 15/320,078

(22) PCT Filed: Jun. 18, 2015

(86) PCT No.: PCT/US2015/036391
§ 371 (c)(1),
(2) Date: Dec. 19, 2016

(87) PCT Pub. No.: WO2015/195889
PCT Pub. Date: Dec. 23, 2015

(65) Prior Publication Data
US 2017/0209575 A1    Jul. 27, 2017

Related U.S. Application Data

(60) Provisional application No. 62/013,814, filed on Jun. 18, 2014.

(51) Int. Cl.
*A61K 41/00* (2020.01)
*A61N 5/06* (2006.01)
*A61N 5/10* (2006.01)

(52) U.S. Cl.
CPC ........ *A61K 41/008* (2013.01); *A61K 41/0057* (2013.01); *A61N 5/062* (2013.01); *A61N 5/10* (2013.01)

(58) Field of Classification Search
None
See application file for complete search history.

(56) References Cited

U.S. PATENT DOCUMENTS

| 2002/0127224 A1 | 9/2002 | Chen et al. |
| 2013/0115295 A1 | 5/2013 | Wang et al. |
| 2013/0289520 A1 | 10/2013 | Febvay et al. |

OTHER PUBLICATIONS

Qian et al. "Mesoporous-Silica-Coated Up-Conversion Fluorescent Nanoparticles for Photodynamic Therapy", small 2009, vol. 5, No. 20, pp. 2285-2290.*
Li et al. "Red long-lasting phosphorescence based on color conversion process", Optical Materials 35 (2013) 451-455, available online Nov. 17, 2012 (Year: 2012).*
International Preliminary Report on Patentability issued in Application No. PCT/US15/36391, dated Dec. 29, 2016.
International Search Report and Written Opinion issued in Application No. PCT/US15/36391, dated Sep. 23, 2015.
Li, et al. "New yellow Ba0.93Eu0.07Al2O4 phosphor for warm-white light-emitting diodes through single-emitting-center conversion", Light-Sci Appl 2013, 2, e50.
Agostinis, et al., "Photodynamic therapy of cancer: an update." CA: a cancer journal for clinicians 61, 2011, 250-281.
Bagshawe, et al., "A cytotoxic agent can be generated selectively at cancer sites", Br. J. Cancer 58, 1988, 700-703.
Bagshawe, et al., "Towards generating cytotoxic agents at cancer sites", Br. J. Cancer 60, 1989, 275-281.
Battelli, et al., "T lymphocyte killing by a xanthine-oxidase-containing immunotoxin", Cancer Immunol. Immunother. 35, 1992, 421-425.
Chen, et al., "Nanoparticles for Improving Cancer Diagnosis", Mat Sci Eng. R. 74, 2013, 35-69.
Gu, et al., "Recent advances in design and fabrication of upconversion nanoparticles and their safe theranostic applications." Adv. Mater. 25, 2013, 3758-3779.
Hughes, et al., "Monoclonal antibody targeting of liposomes to mouse lung in vivo", Cancer Res. 49, 1989, 6214-6220.
Idris, et al., "In vivo photodynamic therapy using upconversion nanoparticles as remote-controlled nanotransducers", Nature Medicine 18, 2012, 1580-1585.
Kim, et al., "Multifunctional Uniform Nanoparticles Composed of a Magnetite Nanocrystal Core and a Mesoporous Silica Shell for Magnetic Resonance and Fluorescence Imaging and for Drug Delivery", Angewandte Chemie 47, 2008, 8438-8441.
Kostron, et al., "Photodynamic Diagnosis and Therapy and the Brain", Methods in Mol. Biol. 635, 2010, 261-280.
Litzinger, et al., "Biodistribution and immunotargetability of ganglioside-stabilized dioleoylphosphatidylethanolamine liposomes", Biochimica et Biophysica Acta, 1104, 1992, 179-187.
Liu, et al., "New Ternary Europium Aluminate Luminescent Nanoribbons for Advanced Photonics", Adv. Funct. Mater. 23, 2013, 1998-2006.
Pietersz, et al., "Antibody Conjugates for the Treatment of Cancer", Reviews, 129, 1992, 57-80.

(Continued)

*Primary Examiner* — James W Rogers
(74) *Attorney, Agent, or Firm* — Meunier Carlin & Curfman LLC

(57) ABSTRACT

Photodynamic therapy systems comprising a nanoparticle that emits electromagnetic radiation having a first wavelength when irradiated with electromagnetic radiation, a photosensitizer which absorbs electromagnetic radiation of said first wavelength and a biocompatible mesoporous material are disclosed herein. In some examples, the photodynamic therapy system comprises a core comprising the nanoparticle, a first shell comprising the biocompatible mesoporous material, and a photosensitizer embedded in the first shell. Upon irradiation by, for example, X-rays, the nanoparticle can function as a transducer, converting X-ray photons to visible photons, and in turn, activating the photosensitizers. Methods of using the photodynamic therapy system are also disclosed.

14 Claims, 15 Drawing Sheets

Specification includes a Sequence Listing.

(56) References Cited

OTHER PUBLICATIONS

Roffler, et al., "Anti-neoplastic glucuronide prodrug treatment of human tumor cells targeted with a monoclonal antibody-enzyme conjugate", Biochem. Pharmacol. 42, 1991, 2062-2065.
Senter, et al., "Generation of 5-fluorouracil from 5-fluorocytosine by monoclonal antibody-cytosine deaminase conjugates", Bioconjugate Chem. 2, 1991, 447-451.
Senter, et al., "Generation of cytotoxic agents by targeted enzymes.", Bioconjugate Chem. 4, 1993, 3-9.
Sternberg, et al., "Porphyrin-based Photosensitizers for Use in Photodynamic Therapy", Tetrahedron 54, 1998, 4151-4202.
Wang, et al., "Upconversion Nanoparticles for Photodynamic Therapy and Other Cancer Therapeutics", Theranostics 3, 2013, 317-330.
Lu et al., Silica encapsulation study on $SrAl2O4:Eu2+,Dy3+$ phophors, Materials Chemistry and Physics, vol. 93, pp. 526-530, 2005.
Extended European Search Report issued in related European Application No. 15810278.0, dated Nov. 30, 2018.

\* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Cys Asp Cys Arg Gly Asp Cys Phe Cys
1               5
```

INDUCED PHOTODYNAMIC THERAPY USING NANOPARTICLE SCINTILLATORS AS TRANSDUCERS

ACKNOWLEDGEMENT OF GOVERNMENT SUPPORT

This invention was made with government support under grant numbers R00 CA153772 awarded by the National Institutes of Health. The government has certain rights in this invention.

FIELD

The disclosed subject matter relates generally to cancer therapy, more particularly to compositions and methods for treating cancer by photodynamic activation of phosensitizers in a tissue affected by a cancerous condition.

BACKGROUND

Photodynamic therapy (PDT) is an emerging treatment modality that has shown promise for many types of disease, including cancer. Compared to other common treatment modalities (e.g., radiotherapy and chemotherapy), PDT is minimally invasive, induces low systematic toxicity, and causes little intrinsic or acquired resistance. One downside of PDT, however, is its inability to treat tumors located deep under the skin, a result of short penetration depth of light in tissues. This problem can be partially compensated with advanced light-delivering technologies that allow for illumination of certain internal cavities, such as the bladder, prostate, lung, and esophagus (Agostinis, P., et al. *Photodynamic therapy of cancer: an update. CA: a cancer journal for clinicians*, 61, 250-281 (2011) and Kostron, H., *Methods in molecular biology*, 635, 261-280 (2010)). Nonetheless, it is considered challenging or impossible for conventional PDT to treat tumors of large volumes or multiple loci. Recently, there have been exciting developments of novel PDT derivatives, such as two-photon PDT or upconversion nanoparticle-mediated PDT, which aim to minimize tissue interference and improve on penetration depth (Wang, C., et al., *Theranostics* 3, 317-330 (2013); Gu, Z., et al. *Adv Mater.*, 25, 3758-3779 (2013); Idris, N. M., et al. *Nature medicine*, 18, 1580-1585 (2012); and Chen, et al., *Mat Sci Eng R*, 74, 35-69 (2013)). But since light is still employed as the energy source, the efficiency of the treatments may still be surface-weighted.

There is a need for photodynamic therapy systems and methods for treating diseases such as tumors, located deep under the skin, a result of short penetration depth of light in tissues. In accordance, the present disclosure addresses these needs.

SUMMARY

In accordance with the purposes of this disclosure, as embodied and broadly described herein, this disclosure, in one respect, relates to a photodynamic therapy system, comprising, a nanoparticle that emits electromagnetic radiation having a first wavelength when irradiated with electromagnetic radiation having a second wavelength (e.g. visible light, near-infrared light, and X-ray), a photosensitizer which absorbs electromagnetic of said first wavelength, and a biocompatible mesoporous material. Methods of using the photodynamic therapy system are also disclosed.

In some examples, the photodynamic therapy system comprises a nanoparticle core surrounded by the mesoporous material, having the photosensitizer dispersed therein. The nanoparticle can be any suitable nanoparticle, including but are not limited to, metallic nanoparticle, organic nanoparticle, hydrolytic nanoparticle, inorganic nanoparticle, ceramic nanoparticle, doped nanoparticle, and any combination thereof. In some further examples, the nanoparticle can be hydrolytic. For example, the nanoparticle can be strontium aluminum oxide doped with a rare earth element such as La, Lu, Ce, Pr, Nd, Sm, Eu, Tb, Dy, Ho, Er, Tm, or Yb in one or more oxidation states. The photosensitizer can be derived from cyanine, porphyrin and their derivatives, pyrrole, tetrapyrrolic compound, expanded pyrrolic macrocycle and their derivatives, flavins, organometallic specie, or any combination thereof. For example, the photosensitizer can be merocyanine 540. Any suitable ionizing radiation can be used to activate the nanoparticle, for example, the ionizing radiation can be X-rays, alpha particles, beta-particles, neutrons, gamma rays, and combinations thereof.

The photosensitizer can be characterized as having an afterglow nanoparticle, a scintillation nanoparticle, a thermoluminescence nanoparticle, a magnetoluminescence nanoparticle, a phosphorescence nanoparticle, a photostimulated luminescence nanoparticle, or a bioluminescence nanoparticle.

The methods disclosed herein can include administering a photodynamic therapeutic composition comprising a biocompatible nanoparticle that emits electromagnetic radiation (such as visible light) having a first wavelength when irradiated with electromagnetic radiation having a second wavelength (e.g. visible light, near-infrared light, and X-ray), a photosensitizer which absorbs electromagnetic radiation having said first wavelength, and a biocompatible mesoporous material, wherein the photosensitizer can be embedded in the mesoporous material; and illuminating the treatment area by irradiation thereby causing the nanoparticles to emit electromagnetic radiation having the first wavelength.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several aspects of the disclosure and together with the description, serve to explain the principles of the disclosure.

FIG. 1A shows an X-ray diffraction (XRD) analysis. The main product was identified as isostructural monoclinic $SrAl_2O_4$ (JCPDS #34-0379). FIG. 1B shows the result from an X-ray near edge structure (XANES). A trace amount of Eu in a divalent oxidation state is present in the product. FIG. 1C is an image of a raw SAO product under 365-nm UV excitation wavelength taken by a digital microscope. Strong green fluorescence was emitted from the material. FIG. 1D is an image of a single SAO wire struck by a narrow X-ray beam (the hit point was circled by red dashed lines). The resulting green emission disseminated to the surroundings or along the wire.

FIG. 2A is a transmission electron microscopy (TEM) image of bare SAO particles. FIG. 2B shows SAO@SiO$_2$ particles. The silica coating is two-layered, comprising of an inner solid layer and an outer mesoporous layer. FIG. 2C is a photoluminescence spectrum of SAO@SiO$_2$ nanoparticles under excitation by light of different wavelengths (300-450 nm). Maximum emission is shown at ~520 nm. FIG. 2D is a XEOL spectrum of SAO@SiO$_2$ nanoparticles. Emission also peaks at ~520 nm. Inset: photograph of SAO@SiO$_2$ nanoparticle powder under X-ray irradiation.

FIGS. 3A and 3B are TEM images at low (FIG. 3A) and high (FIG. 3B) magnification for SAO nanoparticles coated with a layer of solid silica. FIG. 3C shows the size distribution of the solid-silica-coated SAO nanoparticles. FIGS. 3D and 3E are TEM images at low (FIG. 3D) and high (FIG. 3E) magnification for SAO nanoparticles coated with two layers of silica, i.e., SAO@SiO$_2$ nanoparticles. FIG. 3F shows the size distribution of SAO@SiO$_2$ nanoparticles. FIG. 3G shows the fluorescence of SAO nanoparticles, without silica coating.

FIG. 4A shows TEM images taken at different time points. Scale bars, 100 nm. FIG. 4B shows the changes of photoluminescence (ex/em: 365 nm/520 nm). Intensity of photoluminescence drops over time, indicating degradation of SAO nanoparticles. FIG. 4C shows a MTT assay results, studied with hydrolytes of bare SAO nanoparticles (0.05 mg/mL). No cytotoxicity was observed.

FIG. 5A is an absorbance spectrum. FIG. 5B is an X-ray excited luminescent spectrum under X-ray excitation. The spectrometer was coupled with a 285-nm emission filter and the emission slit was set at 3 nm. FIG. 5C is fluorescence emission spectra of SAO under excitation of light of different wavelengths.

FIGS. 6A and 6B are photographs of SAO in powder (FIG. 6A) and aqueous solutions (FIG. 6B, 1 mg/mL) under X-ray irradiation in the dark. Images were taken on a Mastro small animal imager. A mini-X X-ray tube (Amptek Inc.) was set up in the chamber of the imager as the excitation source. FIG. 6C is an X-ray excited optical luminescence spectra of FIGS. 6A and 6B. FIGS. 6D and 6E are photographs of M-SAO@SiO$_2$ nanoparticles under X-ray irradiation, taken by an iPhone 4s.

FIG. 9A shows an overlap of the XEOL of SAO (red) and the absorbance of MC540 (black) particles.

FIG. 9B shows a comparison of singlet oxygen $^1O_2$ production, using SOSG as an indicator (ex/em: 504/525 nm). Increased levels of $^1O_2$ were only observed with M-SAO@SiO$_2$ nanoparticles when they were under X-ray irradiation. Notably, there was 1-min intermission after each 5-min X-ray irradiation cycle. FIG. 9C shows X-PDT induced $^1O_2$ generation in cells. Similar to the observations in FIG. 9B, enhanced 525-nm fluorescence—which signals $^1O_2$ generation—was only observed when cells were treated with M-SAO@SiO$_2$ nanoparticles in the presence of X-ray irradiation. Scale bars: 100 μm. FIG. 9D shows the results from cytotoxicity studies, using ethidium homodimer-1 as dead cell markers (a.k.a dead assay). Correlated to the observations in FIG. 9C, M-SAO@SiO$_2$ nanoparticles plus X-ray caused prominent cell death (ex/em: 530 nm/635 nm). Scale bars, 50 μm. FIG. 9E shows the results from a MTT assay. Cell viability was reduced when cells were treated with the combination of M-SAO@SiO$_2$ nanoparticle and X-ray, and was minimally unaffected in the controls.

FIG. 13A shows the relative changes of tumor volumes (V/V$_0$, n=5). Significant tumor suppression and shrinkage was observed with animals injected with M-SAO@SiO$_2$ nanoparticles and irradiated by X-ray. In all the control groups, tumors grew rapidly and with a comparable pace. By day 14, all the animals in the control groups had either died or been euthanized for meeting at least one humane end point. *P<0.05. FIG. 13B shows photographs of representative tumors from groups 1-6. FIG. 13C shows the relative changes of body weights in each group. No significant decrease of body weight was observed with X-PDT-treated animals. FIG. 13D shows H and E staining on tumors taken from group 1-6. Compared to all the controls, where densely packed neoplastic cells were observed throughout the mass, tumors after X-PDT treatment manifested drastically impacted tumor architectures and significantly reduced cell density, with many regions void of viable cells.

FIG. 16A shows H and E staining with tumor tissues from different groups. FIG. 16B shows H and E staining with normal tissues taken from Group 1.

FIG. 17A shows the strontium (Sr) contents in different organs. The results were based on analysis on tissue samples taken from animals 16 days after intravenous injection of M-SAO@SiO$_2$ nanoparticles (4.25 mg/kg, n=3). Compared to controls (animals not injected with M-SAO@SiO$_2$ nanoparticles), there was no significant increase of Sr levels in all the organs, suggesting that the SAO had been mostly degraded and excreted by day 16. FIG. 17B shows changes in body weight. FIG. 17C shows H and E staining with the spleen, heart, kidneys, and liver. No sign of abnormalities was observed.

FIG. 19A shows the results from ethidium homodimer-1 assay results. Despite the thick pork as obstruction, X-ray can effectively activate X-PDT to cause cell death, manifested by enhanced red fluorescence (ex/em: 530/635 nm). Scale bar: 100 μm. FIG. 19B shows a comparison of cytotoxicity, with and without the use of pork as an X-ray block. No significant difference in viability drop was observed relative to the cells receiving X-PDT but with direct X-ray exposure (35±9% vs. 38±9% for cells treated with and without pork, respectively, P<0.05). This observation confirms the independence of X-PDT to tissue depth.

DETAILED DESCRIPTION

Figures 1A, 1B, 1C, 1D:
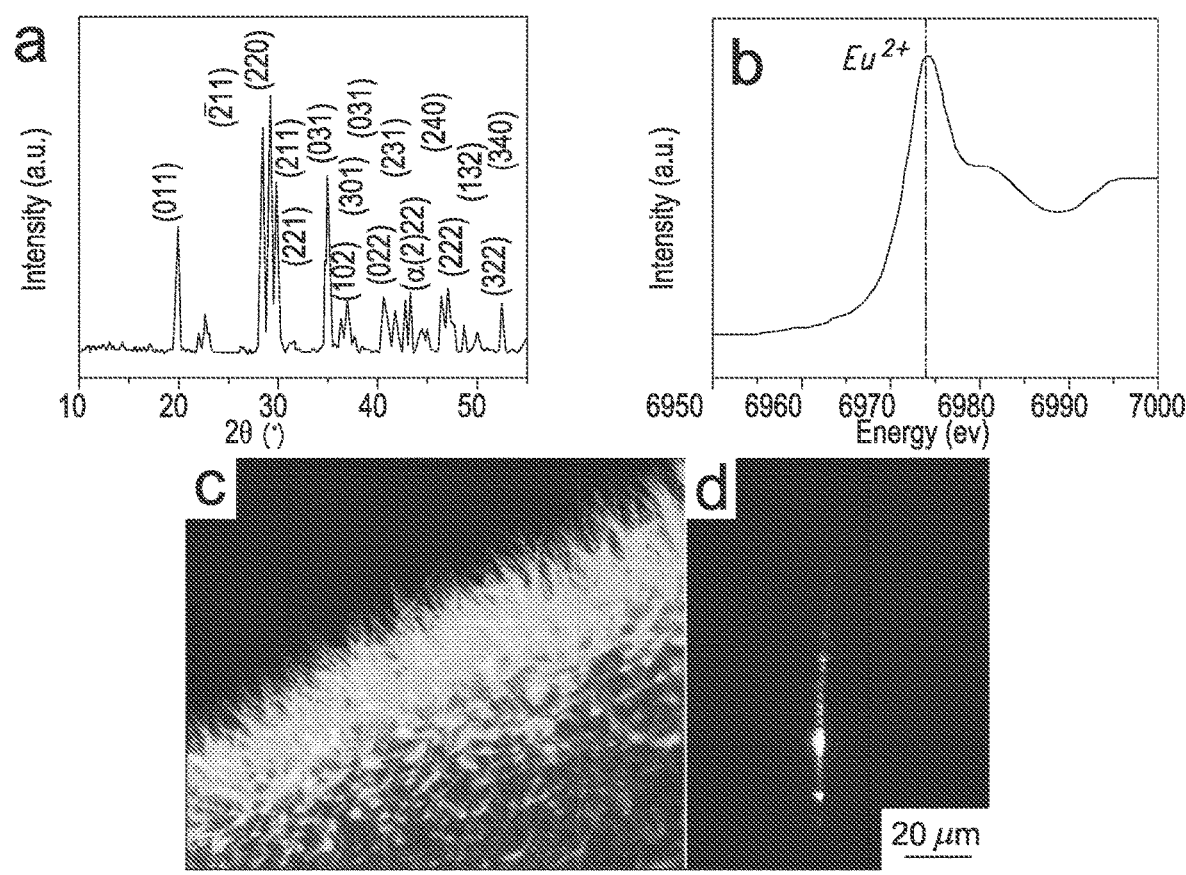
FIGS. 1A-1D show the structure, composition, and optical properties of raw $SrAl_2O_4$:1% $Eu^{2+}$ (SAO).

The present disclosure can be understood more readily by reference to the following detailed description and the Examples included therein and to the Figures and their previous and following description.

As used in the specification and the appended claims, the singular forms "a," "an," and "the" include plural referents unless the context clearly dictates otherwise. Thus, for example, reference to "a photodynamic therapy system" includes mixtures of two or more such systems, reference to "the nanoparticle" includes mixtures of two or more such nanoparticles, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Unless stated to the contrary "about" a particular value means within 5% of the particular value, e.g., within 2% or 1% of the particular value.

Systems

Photodynamic therapy systems are disclosed herein. The photodynamic therapy systems can comprise a nanoparticle that emits electromagnetic radiation having a first wavelength, a photosensitizer that absorbs electromagnetic radiation of said first wavelength, and a mesoporous material having the photosensitizer embedded therein. In some examples, excitation of the nanoparticle by electromagnetic radiation having a second wavelength, such as X-rays, can cause the nanoparticles to emit electromagnetic radiation of a first wavelength. Absorption of the first wavelength by the photosensitizer can activate the photosensitizer to produce singlet oxygen for photodynamic therapy. The disclosed systems can be configured so that the nanoparticle and mesoporous material with photosensitizer can be separate or they can be contained within the same particle, e.g., the mesoporous material with photosensitizer can surround the nanoparticle as a shell. The systems can also contain additional shells that can be located between the nanoparticle and mesoporous material, around both the nanoparticle and mesoporous material, or both between and around the nanoparticle and mesoporous material.

Nanoparticle

The nanoparticle that can be used in the disclosed photodynamic therapy systems should be capable of absorbing radiation and emitting electromagnetic radiation (such as visible light) of a first wave length. The nanoparticle can be metallic nanoparticles, organic nanoparticles, hydrolytic nanoparticles, inorganic nanoparticles, ceramic nanoparticles, doped nanoparticles, and combinations thereof. Generally, the nanoparticle is selected such that, the electromagnetic radiation emitted has a wavelength that overlaps, at least partially, with the absorption spectrum of the photosensitizer. For example, if the photosensitizer is merocyanine 540, the selected nanoparticle can have a maximum emission wavelength of about 520 nm to match the absorption band of merocyanine.

The nanoparticle can be a scintillation nanoparticle. Scintillation nanoparticles, as used herein, refer to nanoparticles that can absorb ionizing radiation such as X-rays, neutrons, alpha, beta, or gamma-rays. Following irradiation, the nanoparticles become excited and the radiative recombination of electron hole pair results in an afterglow of visible light, that is, a scintillation. The nanoparticle can be any form of strontium aluminum oxide $Sr_wAl_xO_y$ doped with a rare earth element (RaE) such as $Eu^{2+}$, $Dy^{3+}$, $Nd^{3+}$, or combinations thereof, wherein the ratio of "y/x" is from 1 to 10 and/or the ratio "w/x" is from 1 to 10 (e.g., $Sr_4Al_{14}O_{25}$, $SrAl_2O_4$, $SrAl_2O_7$, and $Sr_3Al_2O_6$ doped with $Eu^{2+}$, $Dy^{3+}$, $Nd^{3+}$, or combinations thereof). Examples of suitable nanoparticle material include, but are not limited to, any form of strontium aluminum oxide, such as $Sr_aAl_bO_c$, where a, b, and c are integers that can vary; any form of strontium aluminum oxide doped with a rare earth element (RaE), $Sr_aAl_bO_c$:RaE, wherein a, b, and c are integers that can vary and RaE is Ce, Pr, Nd, Sm, Eu, Tb, Dy, Ho, Er, Tm, or Yb in one or more oxidation states, such as Europium(II), Dysprosium(III), or Neodymium(III) doped $Sr_4Al_{14}O_{25}$, $SrAl_2O_4$, $SrAl_2O_7$, and $Sr_3Al_2O_6$; any form of strontium aluminum oxide co-doped with two or more different rare earth elements (RaEs), $Sn_aAl_bO_c:(RaE)_2$, wherein a, b, and c are integers that can vary and RaE is Ce, Pr, Nd, Sm, Eu, Tb, Dy, Ho, Er, Tm, or Yb in one or more oxidation states, such as strontium aluminum oxide co-doped with Europium(II) and Dysprosium(III) as in $Sr_4Al_{14}O_{25}:Eu^{2+}:Dy^{3+}$, $SrAl_2O_4:Eu^{2+}:Dy^{3+}$, $SrAl_2O_7:Eu^{2+}:Dy^{3+}$, and $Sr_3Al_2O_6:Eu^{2+}:Dy^{3+}$; and strontium aluminum oxide co-doped with Europium(II) and Neodymium(III) as in $Sr_4Al_{14}O_{25}:Eu^{2+}:Nd^{3+}$, $SrAl_2O_4:Eu^{2+}:Nd^{3+}$, $SrAl_2O_7:Eu^{2+}Nd^{3+}$, and $Sr_3Al_2O_6:Eu^{2+}:Nd^{3+}$; any form of rare-earth ion-doped gadolinium oxide or oxysulfide phosphor, $Gd_2O_3:RaE^{3+}$ or $Gd_2O_2S:RaE^{3+}$, wherein RaE is Ce, Pr, Nd, Sm, Eu, Tb, Dy, Ho, Er, Tm, or Yb; any rare-earth (RaE) ion co-doped alkaline earth aluminum oxide, $xMO+yAl_2O_2:RaE$, where x and y are integers, and M is Ca, Sr, or Ba, and RaE is Ce, Pr, Nd, Sm, Eu, Tb, Dy, Ho, Er, Tm, or Yb; any rare-earth- or transition-metal-doped metal halide, including, but not limited to, $LaF_3:Ce^{3+}$, $LuF_3:Ce^{3+}$, $CaF_2:Mn^{2+}$, $CaF_2:Eu^{2+}$, $BaFBr:Eu^{2+}$, $BaFBr:Mn^{2+}$, $CaPO_4:Mn^{2+}$, $LuI_3:Ce$, $SrI_2:Eu$, $CaI_2:Eu$, $GdI_3:Ce$; or any other suitable material, such as CdS, CdSe, CdTe, $CaWO_4$, ZnS:Cu, TmO, ZnSe:Te, ZnS, ZnO, $TiO_2$, GaN, GaAs, GaP, InAs, InP, $Y_2O_3$, $WO_3$, and $ZrO_2$. Specific examples of integers for index a can be 1, 2, 3, 4, 5, 6, 7, and 8. Specific examples of integers for index b can be 1, 2, 3, 4, 5, 6, 7, 8, 9, 10, 11, 12, 13, 14, 15, 16, 17, 18, 19, and 20. Specific examples of integers for index c can be 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. These materials can be made by chemical synthesis, solid state reaction, other methods, or any combination thereof.

Representative nanoparticles that can be used in the disclosed photodynamic system include, but are not limited to, any form of strontium aluminum oxide doped with Europium(II), such as $Sr_4Al_{14}O_{25}:Eu^{2+}$, $SrAl_2O_4:Eu^{2+}$, $SrAl_2O_7:Eu^{2+}$, or $Sr_3Al_2O_6:Eu^{2+}$. In some examples, the nanoparticle can be any strontium aluminum oxide co-doped with Europium(II) and Dysprosium(III), such as $Sr_4Al_{14}O_{25}:Eu^{2+}:Dy^{3+}$, $SrAl_2O_4:Eu^{2+}:Dy^{3+}$, $SrAl_2O_7:Eu^{2+}:Dy^{3+}$, or $Sr_3Al_2O_6:Eu^{2+}:Dy^{3+}$.

In some further examples, the nanoparticle can be a semiconductor nanomaterial such as ZnS, ZnO, or $TiO_2$. Other examples of suitable scintillation nanoparticles include, but are not limited to, $CaF_2$, BaFBr, and $CaPO_4$, doped nanoparticles.

The nanoparticle can be a long-afterglow nanoparticle. These nanoparticles are luminescent materials with long decay lifetimes, ranging from a few minutes to tens of hours. Nanoparticles that exhibit both scintillation and afterglow luminescence can also be used with the presently disclosed photodynamic therapy system. When such "afterglow" nanoparticles are used in the photodynamic therapy system, the radiation dose can be greatly reduced. For example, if scintillation nanoparticles without afterglow are used, 30 seconds of radiation dosing may be used to generate enough photons for photodynamic therapy activation; whereas, if scintillation nanoparticles with afterglow are used, only 10 seconds of radiation dosing may be needed to generate enough photons for photodynamic therapy because extra photons are contributed from the afterglow. Therefore, the benefits and applications of nanoparticles having afterglow are tremendous.

In some examples, the nanoparticle can be biocompatible, such that the photodynamic therapy system is suitable for use in a variety of biological applications. "Biocompatible" or "biologically compatible", as used herein, generally refer to compounds or particles that are, along with any metabolites or degradation products thereof, generally non-toxic to cells and tissues, and which do not cause any significant adverse effects to cells and tissues when cells and tissues are incubated (e.g., cultured) in their presence. Some biocompatible nanoparticles are nanoparticles that degrade hydrolytically into nontoxic byproducts. In some embodiments, the biocompatible nanoparticles can be water-soluble and stable in biological environments. Examples of suitable biocompatible nanoparticles include, but are not limited to, strontium aluminum oxide and calcium phosphate nanoparticles. Calcium phosphate nanoparticles are non-toxic and are being developed as a vaccine adjuvant and for targeted gene delivery. They have been approved for human use in several European countries. Doping of the strontium aluminum oxide and calcium phosphate nanoparticles with dopants, for example, $Eu^{2+}$ or $Mn^{2+}$, to manipulate their emission energies or wavelengths is easily accomplished because the radius of $Ca^{2+}$ and $Sr^{2+}$ is close to that of $Mn^{2+}$ and $Eu^{2+}$, which also have the same valence state. $CaF_2$, ZnS, and ZnO are also biologically compatible materials.

Other nanoparticles with a certain level of toxicity, such as CdTe and CdSe nanoparticles can also be used. These nanoparticles can be surface coated with biocompatible material such as silica, alumina, titanium oxide or polymers in order to reduce their toxicity.

The nanoparticle can be an oxide, for example, aluminum oxide, zinc oxide, titanium oxide, zirconium oxide, strontium oxide, silicon oxide, cerium oxide, tin oxide, magnesium oxide, cadmium oxide, copper aluminum oxide, silver oxide, gallium oxide, tantalum oxide, thorium oxide, gold, silver, gadolinium oxide, ytterbium, stannic oxide, calcium tungstate, oxysulfide, cobalt ferrite, and combinations thereof. Representative examples of suitable nanoparticles include, but are not limited to, $SrAl_2O_4:Ce^{3+}$; $SrAl_2O_4:Dy^{3+}$; $LaBO_3:Ce$; $ScBO_3:CeYAlBO_3:Ce$; $YBO_3:Ce$; $Ca_2B_5O_9Cl:Eu$; $xEuO.yNa_2O.zB_2O_3$; $YVO_4$; $YVO_4:Eu$; $YVO_4:Dy$; $YVO_4:SmYVO_4:Bi$; $YVO_4:Bi, Eu$; $YVO_4: Bi, Dy$; $YVO_4:Bi, Sm$; $YVO_4:Tm$; $YVO_4:Bi,Tm$; $MgAl_2O_4:Eu$; $CaAl_2O_4:Eu$; $SrAl_2O_4:Eu$; $BaAl_2O_4:Eu$; $LaMgAl_{11}O_{19}:Eu$; $BaMgAl_{10}O_{17}:Eu$; $BaMgAl_{10}O_{17}:Eu,Mn$; $CaAl_{12}O_{19}:Eu$; $SrAl_{12}O_{19}:Eu$; $SrMgAl_{10}O_{17}:Eu$; $Ba(Al_2O_3)_6:Eu$; $(Ba,Sr)MgAl_{10}O_{17}:Eu,Mn$; $CaAl_2O_4:Eu,Nd$; $SrAl_2O_4:Eu,Dy$; $Sr_4Al_{14}O_{25}:Eu,Dy$; $SrMgSi_2O_7:Eu$; $Ba_2MgSiO_7:Eu$; $BaMg_2Si_2O_7:Eu$; $CaMgSi_2O_6:Eu$; $SrBaSiO_4:Eu$; $Sr_2Si_3O_8.SrCl_2:Eu$; $Ba_5SiO_4Br_6:Eu$; $Ba_5SiO_4Cl_6:Eu$; $Ca_2MgSi_2O_7:Eu$; $CaAl_2Si_2O_8:Eu$; $Ca_{1.5}Sr_{0.5}MgSi_2O_7:Eu$; $(Ca,Sr)_2MgSi_2O_7:Eu$; $Sr_2LiSiO_4F:Eu$; $ZnGa_2O_4:Cr^{3+}$; Ge/Sn substituted $ZnGa_2O_4:Cr^{3+}$; $Zn_3Ga_2Ge_2O_{10}:Cr^{3+}$; $SrMgSi_2O_6:Eu^{2+},Dy^{3+}$; $CaMgSi_2O_6$: $Eu^{2+},Mn^{2+},Pr^{3+}$ and $Ca_2Si_5N_8$: $Eu^{2+},Tm^{3+}$, $Ca_{1.86}Mg_{0.14}ZnSi_2O_7$: $Eu^{2+},Dy^{3+}$; $Ca_{0.2}Zn_{0.9}Mg_{0.9}Si_2O_6$: $Eu^{2+},Mn^{2+},Dy^{3+}$; $LiGa_5O_8:Cr^{3+}$, or combinations thereof.

The emission wavelength and quantum yield of the nanoparticle can be modified by the geometric dimensions (size) of the nanoparticle. Therefore, in the present disclosure, the particle emission wavelength can be controlled to match the absorption band of the photosensitizers by controlling the geometric dimensions of the nanoparticle. The nanoparticle can have geometric dimensions from about 5 nm to about 5000 nm. For example, the nanoparticle can have a geometric dimension of less than about 10 nm, less than about 20 nm, less than about 30 nm, less than about 40 nm, less than about 50 nm, less than about 100 nm, less than about 200 nm, less than about 250 nm, less than about 300 nm, less than about 350 nm, less than about 400 nm, less than about 450 nm, less than about 500 nm, less than about 550 nm, less than about 600 nm, less than about 650 nm, less than about 700 nm, less than about 800 nm, less than about 900 nm, less than about 1000 nm, less than about 1500 nm, or less than about 2000 nm, greater than about 10 nm, greater than about 20 nm, greater than about 30 nm, greater than about 40 nm, greater than about 50 nm, greater than about 60 nm, greater than about 70 nm, greater than about 80 nm, greater than about 90 nm, greater than about 100 nm, greater than about 150 nm, greater than about 200 nm, greater than about 250 nm, greater than about 300 nm, greater than about 350 nm, greater than about 400 nm, greater than about 450 nm, greater than about 500 nm, greater than about 550 nm, greater than about 600 nm, greater than about 650 nm, greater than about 700 nm, greater than about 750 nm, greater than about 800 nm, greater than about 850 nm, greater than about 900 nm, greater than about 950 nm, greater than about 1000 nm, from about 1 nm to about 2000 nm, about 1 nm to about 1500 nm, about 1 nm to about 1000 nm, about 1 nm to about 750 nm, about 1 nm to about 500 nm, about 1 nm to about 300 nm, about 1 nm to about 100 nm, from about 5 nm to about 2000 nm, about 5 nm to about 1500 nm, about 5 nm to about 1000 nm, about 5 nm to about 750 nm, about 5 nm to about 500 nm, about 5 nm to about 300 nm, about 5 nm to about 100 nm, about 50 nm to about 2000 nm, about 50 nm to about 1000 nm, about 50 nm to about 750 nm, about 50 nm to about 650 nm, about 50 nm to about 500 nm, about 100 nm to about 1000 nm, about 100 nm to about 900 nm, about 100 nm to about 800 nm, about 100 nm to about 700 nm, about 100 nm to about 600 nm, about 100 nm to about 500 nm, about 100 nm to about 400 nm, about 200 nm to about 1000 nm, about 200 nm to about 850 nm, about 200 nm to about 750 nm, about 200 nm to about 700 nm, about 200 nm to about 650 nm, about 200 nm to about 600 nm, about 200 nm to about 500 nm, about 200 nm to about 400 nm, about 200 nm to about 350 nm, about 200 nm to about 300 nm, about 250 nm to about 800 nm, about 250 nm to about 750 nm, about 250 nm to about 700 nm, about 250 nm to about 650 nm, about 250 nm to about 600 nm, about 250 nm to about 550 nm, about 250 nm to about 500 nm, about 250 nm to about 450 nm, about 250 nm to about 400 nm, about 300 nm to about 1000 nm, about 300 nm to about 900 nm, about 300 nm to about 800 nm, about 300 nm to about 750 nm, about 300 nm to about 700 nm, about 300 nm to about 650 nm, about 300 nm to about 600 nm, about 300 nm to about 550 nm, about 300 nm to about 500 nm, about 300 nm to about 450 nm, about 300 nm to about 400 nm, or about 300 nm to about 350 nm. The nanoparticles can be spherical or asymmetric.

The emission energy or wavelength can also be adjusted by the use of different dopants in the nanoparticle. The nanoparticle can absorb energy then emits at a preferred wavelength as a result of a dopant ion in the nanoparticle. The nanoparticle can be doped with at least one rare earth element or lanthanide such as La, Ce, Pr, Nd, Pm, Sm, Eu, Gd, Tb, Dy, Ho, Er, Tm, Yb, or Lu, any one if which can be at various oxidation states. The amount of dopant ion in the nanoparticle can be in an amount greater than about 0.1 wt %, greater than about 0.3 wt %, greater than about 0.5 wt %, greater than about 0.7 wt %, greater than about 0.9 wt %, greater than about 1 wt %, greater than about 1.5 wt %, greater than about 2 wt %, less than about 0.2 wt %, less than about 0.5 wt %, less than about 0.7 wt %, less than about 1 wt %, less than about 1.5 wt %, less than about 2 wt %, less than about 2.5 wt %, less than about 5 wt %, or less than about 10 wt %.

The emission energy can be further enhanced by dielectric confinement. If the dielectric constant (c) of the nanoparticles is greater than that of the surrounding matrix, the electric force lines of the particles will penetrate into the matrix, and the Coulomb interaction will be enhanced. As a consequence, the binding energy and the oscillator strength of the exciton are greatly increased. This is called dielectric confinement. This effect can be used to further enhance the emission energy and stability of the nanoparticles. ZnO (c=1.7) and $SiO_2$ (c=3.9) are suitable materials as their dielectric constants are lower than the CdS (c=9.12), ZnS (c=8.2), $CaF_2$ (c=6.76), BaFBr (c=14.17), and $CaPO_4$ (c=14.5) nanoparticles. Thus, when these nanoparticles are coated with ZnO or $SiO_2$ to form core/shell structures, they have very high luminescence quantum efficiencies as a result of quantum size confinement and dielectric confinement. In addition, coating with ZnO or $SiO_2$ can increase the stability and reduce the toxicity of the nanoparticles. For example, coating $CaF_2:Eu^{2+}$ nanoparticles with $SiO_2$ prevents the oxidation of $Eu^{2+}$ to $Eu^{3+}$ by singlet oxygen. This will not only protect the nanoparticles but also improve the photodynamic therapy system's efficiency because the coating prevents the trapping of singlet oxygen by $Eu^{2+}$ ions. The coating of CdS nanoparticles with $SiO_2$ or ZnO also reduces their toxicity because the coating prevents the leaking of $Cd^{2+}$, which is toxic. However, the coating layer (shell) should be thinner than the energy transfer critical distance so that it does not block the energy transfer from the nanoparticles to the photosensitizers For example, the shell thickness can have a geometric dimension of less than about 5 nm, less than about 10 nm, less than about 20 nm, less than about 30 nm, less than about 40 nm, less than about 50 nm, less than about 100 nm, less than about 200 nm, less than about 250 nm, less than about 300 nm, less than about 350 nm, less than about 400 nm, less than about 450 nm, less than about 500 nm, less than about 550 nm, less than about 600 nm, less than about 650 nm, less than about 700 nm, less than about 800 nm, less than about 900 nm, less than about 1000 nm, less than about 1500 nm, or less than about 2000 nm, greater than about 10 nm, greater than about 20 nm, greater than about 30 nm, greater than about 40 nm, greater than about 50 nm, greater than about 60 nm, greater than about 70 nm, greater than about 80 nm, greater than about 90 nm, greater than about 100 nm, greater than about 150 nm, greater than about 200 nm, greater than about 250 nm, greater than about 300 nm, greater than about 350 nm, greater than about 400 nm, greater than about 450 nm, greater than about 500 nm, greater than about 550 nm, greater than about 600 nm, greater than about 650 nm, greater than about 700 nm, greater than about 750 nm, greater than about 800 nm, greater than about 850 nm, greater than about 900 nm, greater than about 950 nm, greater than about 1000 nm, from about 1 nm to about 2000 nm, about 1 nm to about 1500 nm, about 1 nm to about 1000 nm, about 1 nm to about 750 nm, about 1 nm to about 500 nm, about 1 nm to about 300 nm, about 1 nm to about 100 nm, about 50 nm to about 2000 nm, about 50 nm to about 1000 nm, about 50 nm to about 750 nm, about 50 nm to about 650 nm, about 50 nm to about 500 nm, about 100 nm to about 1000 nm, about 100 nm to about 900 nm, about 100 nm to about 800 nm, about 100 nm to about 700 nm, about 100 nm to about 600 nm, about 100 nm to about 500 nm, about 100 nm to about 400 nm, about 200 nm to about 1000 nm, about 200 nm to about 850 nm, about 200 nm to about 750 nm, about 200 nm to about 700 nm, about 200 nm to about 650 nm, about 200 nm to about 600 nm, about 200 nm to about 500 nm, about 200 nm to about 400 nm, about 200 nm to about 350 nm, about 200 nm to about 300 nm, about 250 nm to about 800 nm, about 250 nm to about 750 nm, about 250 nm to about 700 nm, about 250 nm to about 650 nm, about 250 nm to about 600 nm, about 250 nm to about 550 nm, about 250 nm to about 500 nm, about 250 nm to about 450 nm, about 250 nm to about 400 nm, about 300 nm to about 1000 nm, about 300 nm to about 900 nm, about 300 nm to about 800 nm, about 300 nm to about 750 nm, about 300 nm to about 700 nm, about 300 nm to about 650 nm, about 300 nm to about 600 nm, about 300 nm to about 550 nm, about 300 nm to about 500 nm, about 300 nm to about 450 nm, about 300 nm to about 400 nm, or about 300 nm to about 350 nm.

Photosensitizer

The systems can also contain a photosensitizer useful for causing photodynamic damage cells. Damage, as used herein, includes destruction of cellular organelles and subsequently suppression of cell growth, suppression of cell growth rate, and/or cell death. In some examples, the emission spectra of the nanoparticles can be matched to the absorption spectra of the photosensitizers. Upon absorption of electromagnetic radiation, the photosensitizer molecules are excited to a short-lived singlet state. Following excitation, fast radiationless relaxation to the lower-lying triplet states occurs via intersystem crossing and ultimately yields the first excited triplet state Ti in a spin-allowed process. The longer the decay lifetime of the triplet state, the more time the photosensitizer has to act on a tissue, such as a tumor tissue and to initiate biochemical and biophysical mechanisms, which cause tumor necrosis. Therefore a long triplet lifetime (>500 ns) can be considered a precondition for efficient photosensitization.

The photosensitizer can be a macrocyclic organic complex, which absorbs radiation in the range of from about 300 nm to about 900 nm, typically from about 400 nm to about 800 nm. These photosensitizers are capable of transferring their absorbed energy to molecular oxygen to generate singlet oxygen. Examples of suitable macrocyclic organic complexes include, but are not limited to, porphyrin and their derivatives, pyrrole, tetrapyrollic compound, expanded pyrrolic macrocycle and their derivatives, cyanine and their derivatives, flavin, organometallic species, nanoparticle, or combinations thereof. Representative examples of suitable macrocyclic compounds include, but are not limited to, green porphyrins, protoporphyrin, chlorins, tetrahydrochlorins (chlorins bacteriochlorins, isobacteriochlorins), hematoporphyrin, benzoporphyrin, texaohyrins, chlorophylls, dyes, aminolevulinic acid (ALA), silicon phthalocyanine Pc 4, m-tetrahydroxyphenylchlorine (mTHPC), mono-L-aspartyl chlorine (Npe6), pyropheophosphides, purpurins, texaphyrins, phenothiaziniums, phthalocyanines, napthalocyanines, porphycenes, pheophorbides, merocyanine, phthalocyanine, chloroaluminum phthalocyanine, sulfonated aluminum phthalocyanine, ring-substituted cationic phthalocyanine, disulfonated or tetrasulfonated derivative, sulfonated aluminum naphthalocyanine, naphthalocyanine, tetracyanoethylene adduct, crystal violet, azure β chloride, benzophenothiazinium, benzophenothiazinium chloride (Et-NBS), phenothiazine derivative, rose Bengal, toluidine blue derviatives, toluidine blue O (TBO), methylene blue (MB), new methylene blue N (NMMB), new methylene blue BB, new methylene blue FR, 1,9-dimethylmethylene blue chloride (DMMB), methylene blue derivatives, methylene green, methylene violet Bernthsen, methylene violet 3RAX, Nile blue, Nile blue derivatives, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, thionine, or combination thereof. Photosensitizers currently approved by the FDA for photodynamic therapy, such as Photofyrin (actually a mixture of porphyrins, including photoporphyrin, haematoporphyrin, hydroxyethyldeuteropophyrin); and verteporfin, a benzoporphyrin, can also be used in the compositions.

The photosensitizers can contain metal cations. The metal ion present in the photosensitizer can be a diamagnetic metal. The metal ion present in the photosensitizer can be a diamagnetic metal. Suitable diamagnetic metals include, but are not limited to aluminum, copper, zinc, tin, silicon, germanium, lithium, magnesium, platinum, palladium, iridium, rudinium, ruthenium, rhenium, osmium, technetium, and combinations thereof. Suitable examples of metal-containing photosensitizers include, but are not limited to, zinc phthalocyanine, sulfonated aluminum phthalocyanine, and magnesium phthalocyanine, and zinc tetraphenyl porphyrin. In some examples, the photosensitizer is not covalently linked to the mesoporous material.

Some nanoparticles can be photoactivated to produce singlet oxygen. These photoactivated nanoparticles can be used in the compositions. Nanoparticle photosensitizers have some advantages in that, they can be made hydrophilic, they possess relatively large surface area, owing to their sub-cellular and nanometer size, nanoparticles can penetrate deep into tissue through fine capillaries and pass through the fenestrae into the epithelial lining so that they can be taken up efficiently by cells, they have high extinction or absorption coefficients, and they are photostable for in vivo applications. Examples of suitable nanoparticles that can be used as a photosensitizer include, but are not limited to, CdTe, CdS, ZnO, $TiO_2$, and Si nanoparticles.

The selection of nanoparticle and photosensitizer can be in a manner to promote energy transfer from the nanoparticles to the photosensitizers thereby ensuring efficient photoactivation. In some embodiments, the energy transfer between the nanoparticle and photosensitizer can be via fluorescence resonance energy transfer (FRET). As used here, FRET refers to the transfer from the initially excited donor (the scintillation nanoparticle) to an acceptor (the photosensitizer). For efficient energy transfer, the emission band of the donor must overlap effectively with the absorption band of the acceptor, and/or the donor and the acceptor must be close enough spatially to permit transfer. FRET energy transfer rate is highly dependent on the distance between the donor and receptor. The distance at which FRET is 50% efficient is called the Förster distance, typically about 2-10 nm. Generally, in order to have an efficient energy transfer, the distance between the donor and the acceptor may be less than about 10 nm. In some examples, the photosensitizer is embedded in a coating around the nanoparticle coating. A description for making the photodynamic therapy system disclosed herein, is discussed below.

First Shell

In some examples, the disclosed photodynamic therapy system can contain a first shell, which can surround the nanoparticle. The first shell can be formed from a mesoporous material. In some examples, the photosensitizer can be embedded in the mesoporous material. In some examples, the photosensitizer can be covalently or non-covalently embedded in the mesoporous material. The mesoporous material can be any suitable biocompatible material. For example, the mesoporous material can be derived from silica, zinc oxide, aluminum oxide, iron oxide, iron hydride, manganese oxide, magnesium oxide, nickel hydroxide, or zirconium oxide. In some examples, the photodynamic therapy system can contain a core comprising a nanoparticle having an emission spectrum when excited by radiation; a first shell comprising a biocompatible mesoporous material, wherein the shell comprises a photosensitizer dynamic therapy drug having an absorption spectrum embedded therein.

The thickness of the first shell surrounding the nanoparticle can be from about 5 nm to about 1000 nm. For example, the thickness of the first shell can be less than about 10 nm, less than about 20 nm, less than about 30 nm, less than about 40 nm, less than about 50 nm, less than about 100 nm, less than about 200 nm, less than about 250 nm, less than about 300 nm, less than about 350 nm, less than about 400 nm, less than about 450 nm, less than about 500 nm, less than about 550 nm, less than about 600 nm, less than about 650 nm, less than about 700 nm, less than about 800 nm, less than about 900 nm, less than about 1000 nm, greater than about 10 nm, greater than about 20 nm, greater than about 30 nm, greater than about 40 nm, greater than about 50 nm, greater than about 60 nm, greater than about 70 nm, greater than about 80 nm, greater than about 90 nm, greater than about 100 nm, greater than about 150 nm, greater than about 200 nm, greater than about 250 nm, greater than about 300 nm, greater than about 350 nm, greater than about 400 nm, greater than about 450 nm, greater than about 500 nm, greater than about 550 nm, greater than about 600 nm, greater than about 650 nm, greater than about 700 nm, greater than about 750 nm, greater than about 800 nm, greater than about 850 nm, greater than about 900 nm, or greater than about 950 nm.

Second Shell

Figure 21:
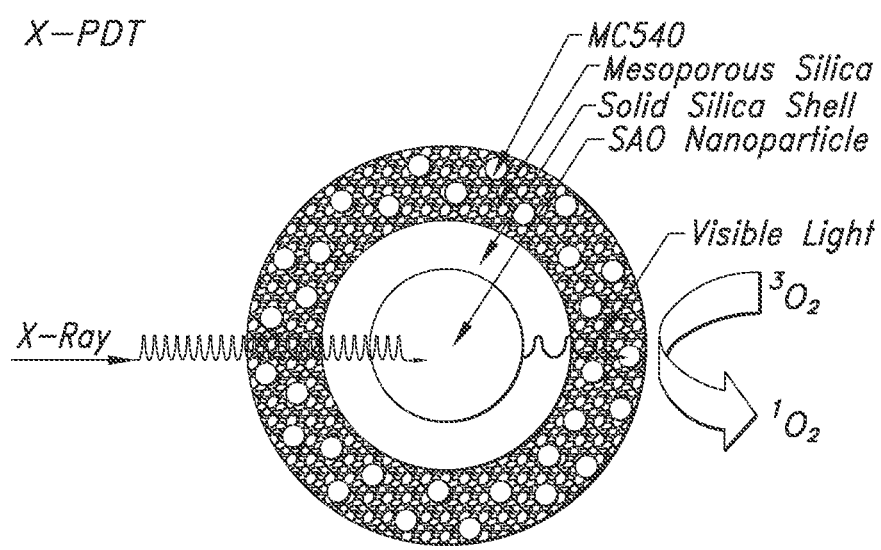
FIG. 21 is a schematic illustration of the working mechanism of X-PDT. A nanoscintillator made of SAO is coated with two layers of silica—an inner solid layer and an outer mesoporous layer. Into the mesoporous silica coating, a photosensitizer, MC540, is loaded. Under X-ray irradiation, SAO converts X-ray to visible light photons. The visible light photons, in turn, activate near-by MC540 molecules to produce cytotoxic $^1O_2$.

In some other examples, the photodynamic therapy system can contain a second shell. The second shell can be a solid layer or coating directly in contact with and immediately surrounding the nanoparticle, and it can itself be surrounded by the first shell (see e.g., FIG. 21). Or the second shell can surround the first shell, which is in direct contact with and immediately surrounds the nanoparticle. The second shell can be used to improve the nanoparticle stability. For example, in instances where the nanoparticle is hydrolytic, a second shell around the nanoparticle can be used to prevent early dissolution of the nanoparticle. As an example, strontium aluminum oxide can be completely degraded in 5 min when directly exposed to aqueous solutions. With a solid silica coating, the lifetime of the strontium aluminum oxide nanoparticles in aqueous solutions can be extended up to about 7 days. The coated nanoparticle, e.g., the silica coated strontium aluminum oxide nanoparticles, can maintain the strong photoluminescence and X-ray excited optical luminescence (XEOL).

In some examples, the second shell can be derived from $SiO_2$, ZnO, gold, silver, aluminum oxide, iron oxide, iron hydride, manganese oxide, magnesium oxide, nickel hydroxide, zirconium oxide, or any other suitable biocompatible material. The thickness of the layer surrounding the nanoparticle can be from about 1 nm to about 1000 nm. For example, the thickness of the layer surrounding the nanoparticle can be less than about 10 nm, less than about 20 nm, less than about 30 nm, less than about 40 nm, less than about 50 nm, less than about 100 nm, less than about 200 nm, less than about 250 nm, less than about 300 nm, less than about 350 nm, less than about 400 nm, less than about 450 nm, less than about 500 nm, less than about 550 nm, less than about 600 nm, less than about 650 nm, less than about 700 nm, less than about 800 nm, less than about 900 nm, less than about 1000 nm, greater than about 10 nm, greater than about 20 nm, greater than about 30 nm, greater than about 40 nm, greater than about 50 nm, greater than about 60 nm, greater than about 70 nm, greater than about 80 nm, greater than about 90 nm, greater than about 100 nm, greater than about 150 nm, greater than about 200 nm, greater than about 250 nm, greater than about 300 nm, greater than about 350 nm, greater than about 400 nm, greater than about 450 nm, greater than about 500 nm, greater than about 550 nm, greater than about 600 nm, greater than about 650 nm, greater than about 700 nm, greater than about 750 nm, greater than about 800 nm, greater than about 850 nm, greater than about 900 nm, or greater than about 950 nm.

Target Recognition Moiety

The specificity of the disclosed photodynamic therapy system can be increased by conjugation of the system with a target recognition moiety, which specifically binds to a component on the surface of, for example, a target cell or tissue. Target recognition moiety includes cell recognition moieties which specifically bind to receptors on the surface of a target cell. Steinberg, E. D., et al., *Tetrahedron*, 54, 4151-4202 (1998) discloses the design of new generations of photosensitizers for the treatment of tumors, the disclosure of which is incorporated herein by reference in its entirety for teachings of various cell recognition moieties. In the disclosed compositions, the cell recognition moiety can typically be present on photodynamic therapy system, e.g., the protein cage.

A wide variety of natural and synthetic molecules recognized by target cells can be used as the cell recognition moiety. Suitable cell recognition moieties include, but are not limited to, a receptor, ligand, polynucleotide, peptide, polynucleotide binding agent, antigen, antibody, or combinations thereof. In one embodiment, the cell recognition moiety is a peptide which has a length of from about 6 amino acids to about 25 amino acids. More specifically, the peptide amino acid sequence can be Cys-Asp-Cys-Arg-Gly-Asp-Cys-Phe-Cys (SEQ ID NO:1), which interacts with integrin $\alpha_v\beta_3$. Integrin $\alpha_v\beta_3$ is overexpressed on tumor vasculatures and tumor cells.

The cell recognition moiety, for example the peptide amino acid sequence, can be similar, homologous, or a variant of cell recognition moieties in the art. In general, variants of the cell recognition moiety for example nucleic acids and peptides herein disclosed, can have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% similarity, or homology, to the stated sequence or the native sequence. Those of skill in the art readily understand how to determine the similarity of two polypeptides or nucleic acids. For example, the similarity can be calculated after aligning the two sequences so that the similarity is at its highest level. As an example, peptides can have one or more conservative amino acid substitutions. These conservative substitutions are such that a naturally occurring amino acid is replaced by one having similar properties. Such conservative substitutions do not alter the function of the peptide.

The following references discloses antibodies, receptors, or receptor ligands that can be used to target specific proteins to tumor tissue: (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, Immunolog. Reviews, 129:57-80, (1992); and Roffler, et al., *Biochem. Pharmacol*, 42:2062-2065, (1991)), disclosure of which are incorporated herein by reference. The following references discloses vehicles such as "stealth" and other antibody conjugated particles (including lipid mediated drug targeting to colonic carcinoma), receptor mediated targeting through cell specific ligands, lymphocyte directed tumor targeting, and highly specific therapeutic retroviral targeting of murine glioma cells in vivo: (Hughes et al., *Cancer Research,* 49:6214-6220, (1989); and Litzinger and Huang, *Biochimica et Biophysica Acta,* 1104:179-187, (1992)), disclosure of which are incorporated herein by reference.

Pharmaceutical Compositions

The systems disclosed herein can be prepared as or formulated into a pharmaceutical composition. For example, the systems can further comprise a pharmaceutically acceptable excipient. The pharmaceutically-acceptable excipient can be administered with the photodynamic therapy system disclosed above. The pharmaceutical compositions can be administered in vivo in a pharmaceutically acceptable carrier. By "pharmaceutically acceptable" is meant a material selected to minimize any degradation of the active ingredient and to minimize any adverse side effects in the subject, as would be well known to one of skill in the art.

Suitable carriers and excipients are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi permeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

The compositions can be administered orally, parenterally (e.g., via intravenous injection, intraperitoneal injection, by intramuscular injection, intratumoral injection, intraarterial injection, transdermally, extracorporeally, topically or the like, including topical intranasal administration or administration by inhalant, or a combination thereof. As used herein, "topical intranasal administration" means delivery of the compositions into the nose and nasal passages through one or both of the nostrils and can comprise delivery by a spraying mechanism or droplet mechanism, or through aerosolization of the compositions. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be desirable.

Pharmaceutical compositions can further include one or more active ingredients such as antimicrobial agents, anti-inflammatory agents, anesthetics, and the like.

Methods of Making

The nanoparticle can be synthesized through a vapor-phase deposition method. For example, for the synthesis of strontium aluminum oxide, $SrCO_3$, $Al_2O_3$, $Eu_2O_3$, and graphite powders can be mixed and heated in a tube furnace system at 1450° C. for 2 h. The reaction may be conducted under an argon flow with pressure maintained at about 5 Torr. The main product can then be identified, i.e., isostructural monoclinic $SrAl_2O_4$ in the present case. The product can then be doped with a trace amount of divalent state Eu. The dimensions, for e.g., the bulkiness of the nanoparticle can be modified, by mechanically ground, followed by sedimentation, filtration and centrifugation, to yield nanoparticles. The size of the nanoparticles can be about 150 nm.

The nanoparticles can then be coated with a shell (first and/or second shell) to host the photosensitizer, improve the nanoparticle stability, enhance luminescence, reduce toxicity, and/or enhance the photodynamic therapy system efficiency. There are a number of different ways of coating the nanoparticles. By way of example, the core nanoparticles may be placed in a silica containing or gallium-containing or aluminum-containing chemical bath for defined period of time. Alternatively, the core nanoparticles may be coated by atomic layer deposition (ALD). The metal layers can be deposited in a fairly conformal, nearly uniform fashion through either chemical bath deposition, electroless plating, or atomic layer deposition, or combinations of these and/or similar techniques.

In some examples, the nanoparticle can be coated with $SiO_2$. In one exemplary method of making the coated nanoparticle, the nanoparticle can be incubated in a mixture of $SiO_2$ source such as tetraethylorthosilicate (TEOS) in ethanol and ammonia, at room temperature. The mesoporous shell can be formed by mixing the resulting silica-coated nanoparticles with a template for the formation of mesopores in the emesoporous later. An exemplary template is cethyltrimethylammonium bromide (CTAB). TEOS can then be added to the CTAB-modified silica coated nanoparticles. CTAB can be removed by adding HCl and heating.

The photosensitizer can be loaded into the mesoporous layer of the coated nanoparticles by mixing the coated nanoparticles into a solution containing the photosensitizer. The nanoparticles can then be collected by centrifugation, followed by washing to remove any unbound photosensitizer.

Methods of Using

The disclosed systems, and compositions comprising them, can be administered to an individual to kill endogenous tissue or cells. The tissue can be undesirable tissue that has arisen due to transformation, such as a tumor, cancer, or endometriosis; adipose tissue; plaques present in vascular tissue and over-proliferation such as those formed in restenosis; birthmarks and other vascular lesions of the skin; scars and adhesions; and irregularities in connective tissue or bone, such as bone spurs. As used herein, the term "cancer" includes a wide variety of malignant solid neoplasms. These can be caused by viral infection, naturally occurring transformation, or exposure to environmental agents. Parasitic infections and infections with organisms, especially fungal, that lead to disease may also be targeted. The compositions can also be used to permeabilize the endothelium and/or vasculature system in tumors to improve the enhanced permeable and retention (EPR) effect in tumor cells.

In some examples, the photodynamic therapy system can be useful for causing photodynamic damage to cancer cells. Photodynamic damages to cancer cells include, but are not limited to, preventing or reducing the development of a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis or increasing the amount of apoptotic cancer cells, thereby treating cancer.

Generally, the methods can include contacting a cell with an effective amount of the photodynamic therapy system or a pharmaceutical composition as described herein. One of skill in the art recognizes that an amount can be considered therapeutically effective even if the condition is not totally eradicated but improved partially. The compositions can be injected directly into the target tissue, or can be administered systemically. More specifically, the compositions can be administered using any suitable method including intravenous (i.v.), intraperitoneal (i.p.), intramuscular (i.m.), intratumoral (i.t), intraarterial (i.a.), topically, and/or inhalation. Intravenous administration is particularly preferred for solid tumors, while i.p. administration is preferred for pancreatic, liver, and gastric tumors. Advantageously, even when administered systemically, the compositions preferentially accumulate in the cancerous tissue, and preferably actively integrate in the cancerous tissue, as opposed to surrounding healthy tissue.

The disclosed methods can also include the application of external ionizing radiation for the purpose of exciting the core of the nanoparticle. The rate and time the cancerous cells are irradiated may depend on the results required. For example, the cells can be irradiated at an effective fluence rate and time to cause permeabilization of the endothelial lining of the cancerous cells, i.e., increase in the Enhanced Permeabilization and Retention (EPR) effect without causing significant occlusion and/or collapse to tumor blood vessels. The cancerous cells can be irradiated at an effective fluence rate and time to cause therapeutic injury resulting in the reduction of at least one of the surface area, the depth, and the amount of the tissue affected by the cancerous condition. The irradiation regime may also be dependent on the compositions and design of the nanoparticle core and shell, the maximum safe dose of radiation that can be tolerated by the patient, or the targeted cell or material.

Irradiation can be any form of excitation radiation, including high-energy particles and radiation from all regions of the electromagnetic spectrum; ultrasound, electric fields and magnetic fields. In some embodiments, irradiation can be carried out using X-ray. X-ray is an energy source widely used in the clinic for both diagnosis and therapy purposes. X-ray can be given to cover either a small area (e.g. in dental radiography) or a large area (chest X-ray and CT). Both types may be employed herein. While narrow-beam X-ray can induce more focal and selective damage, X-ray covering a large area can permit the disclosed system to treat tumors of multiple loci or tumor metastasis. X-rays are advantageous because of both their ability to penetrate through the entire body and the amount of energy contained within the x-ray photon. The X-ray wavelengths can be less than about 10 nanometers, or from about 10 to about 0.01 nm. The power/fluence rate can be about 1 Sv/h or less. Typically, the fluence rate is from about 0.5 Sv/hr to about 1 Sv/hr. The cancerous/tumor cells can be irradiated for any period from about 5 minutes to about 60 minutes, or from about 15 minutes to about 30 minutes. X-ray devices that may be used in the methods herein include conventional commercial x-ray units commonly used for diagnostic or therapeutic purposes, computed-tomography (CT) scanners, full-body scanners or even X-ray lasers.

Other high-energy sources, such as gamma rays, and high-energy particles can also be used. A suitable range of gamma-ray radiation is an amount sufficient to pierce the human body and excite the nanoparticle material. Electromagnetic radiation in the wavelength range of 0.01 to 0.00001 nm is typically considered gamma radiation. High-energy particles include positrons, such as those used in positron emission tomography (PET) scans, and high-energy protons and electrons and are useful as external sources of energy.

The methods can also include the transfer of energy from the nanoparticle to the photosensitizer. One method of such energy transfer can be frequency resonance energy transfer (FRET), which is achieved when the emission spectrum of the core material overlaps the absorption spectrum of the photosensitizer, allowing plasmon excitation.

In some examples, the methods can include removing the nanoparticle or portion thereof, from the body. In such cases, the nanoparticle can be decorated or doped with magnetic material, typically on the surface, to allow magnetic removal of the particle from the blood by established cell-separation techniques.

In one example, the methods include administering a photodynamic therapeutic composition comprising a biocompatible nanoparticle that emits light having a first wavelength when irradiated with electromagnetic radiation (e.g. visible light, near-infrared light, and X-ray), a photosensitizer which absorbs light of said first wavelength, and a biocompatible mesoporous material, wherein the photosensitizer is embedded in the mesoporous material; and illuminating the treatment area by irradiation thereby causing the nanoparticles to emit light of the first wavelength.

Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

All the animal studies conformed to the Guide for the Care and Use of Laboratory Animals published by the National Institutes of Health, USA, and a protocol approved by the Institutional Animal Care and Use Committee (IACUC), University of Georgia. Animal models were established by subcutaneous injection of $10^6$ U87MG onto the hind legs of 5-6 week athymic nude mice (Harlan).

Quantitative data were expressed as mean±standard deviation. A two-tailed Student's t-test was used for statistically comparing the treatment group and the control group. P<0.05 was considered statistically significant.

SAO Nanoparticle Synthesis, Surface Modification, and Photosensitizer Loading

SAO nanoparticles were synthesized by the carbo-thermal reduction and vapor-phase deposition method, discussed in Liu, F., et al., *Adv Funct Mater* 2013, 23:1998-2006 and Li, X. F., et al. *Light-Sci Appl* 2013, 2. Briefly, $SrCO_3$, $Al_2O_3$, $Eu_2O_3$, and graphite powders were mixed and heated in a tube furnace system at 1450° C. for 2 h. The reaction was conducted under an argon flow with pressure maintained at about 5 Torr.

To render SAO amenable to bio-related applications, bulk SAO was ground to particles of c.a. 150 nm. These bare SAO nanoparticles were coated with a layer of solid silica. The resulting nanoparticles were subsequently coated with a layer of mesoporous silica, except that 3-aminopropyltriethoxysilane (5%) was mixed with tetraethyl orthosilicate (TEOS) as a silane precursor.

Characterizations of SAO Particles

UV-vis absorption spectra were recorded on a Shimdzu 2450 UV-Vis spectrometer. Photoluminescence measurements were performed on a Hitachi F-7000 fluorometer. X-ray excited optical luminescence (XEOL) was measured on Horiba Jobin Yvon FL3-2iHR fluorescence spectrometer using an emission filter of 285 nm and an emission slit of 3 nm. A mini-X X-ray tube (Amptek Inc.) was used as the X-ray source, and was set at 25 kV and 120 µA for the irradiation. The recorded spectrum was smoothed by a Savitzky-Golay method of 5 points. TEM and HR-TEM samples were prepared by dripping sample solutions onto carbon-coated copper grids and evaporating the solvent. The TEM/HR-TEM images were taken on an FEI Tecnai 20 transmission electron microscope operating at 200 kV. Dynamic light scattering (DLS) analysis was performed using a Zetasizer Nano S90 size analyzer (Malvern Corp, U.K.).

Loading MC540 onto SAO@SiO$_2$ Nanoparticles

For MC540 loading, MC540 in ethanol was added to an aqueous solution of SAO@SiO$_2$ nanoparticles. The mixture was incubated overnight at room temperature. The mixture was then centrifuged and the supernatant removed. The collected nanoparticles were resuspended in PBS. The MC540 content in the supernatant was quantified by UV-vis analysis and comparing to a pre-determined standard curve. This number was deduced from the mass of MC540 added at the beginning to yield the amount of MC540 that was loaded onto SAO@SiO$_2$ nanoparticles. The loading efficiency in wt % was computed using Equation 1:

$$\text{Photosensitizer loading (\%)} = \frac{\text{Mass of photosensitizers incorporated into particles}}{\text{Mass of particles}} \times 100 \quad (1)$$

X-Ray-to-Visible Conversion Efficiency (Y) of SAO

The fundamental limit of the light conversion efficiency (Y) of SAO (photons emitted per MeV) is determined by the band gap $E_{gap}$ (eV) of XEOL based on Equation 2:

$$Y = \frac{10^6}{2.5 E_{gap}} \quad (2)$$

Previous reports showed that $E_{gap}$ of $SrAl_2O_4$:Eu is about 5.18 eV[8-11]. It is thus deduced that the fundamental limit of optical photon yield for SAO is ~77,000 optical photons per MeV. Given that each 512 nm photon carries energy of 2.384 eV, the approximate $$\text{Efficiency in energy conversion (\%)} = \frac{77000 \times 2.384 \text{ eV}}{10^6 \text{ eV}} = 18.4\%$$

Energy Transfer Efficiency

The energy transfer efficiency is measured by comparing the fluorescence intensity of SAO@SiO$_2$ nanoparticles without ($F_0$) and with (F) loading of MC540 based on Equation 3:

$$E = 1 - \frac{F}{F_0} \quad (3)$$

It was shown that E was 66.7% for M-SAO@SiO$_2$ nanoparticles.

$^1O_2$ Production in Solutions 1 mL of 0.05 mg M-SAO@SiO$_2$/mL was added in a quartz cuvette (equilibrated with air at room temperature) containing 1 µM of SOSG. For controls, SAO, MC540, and water were analyzed. The solutions were irradiated by X-ray (at an irradiance of 1 Sv/h for 20 min, with a 1-min intermission after each 5-min irradiation cycle. The fluorescence signals (ex/em: 504/525 nm) were measured on a Hitachi F-7000 fluorescence spectrophotometer.

Comparison of $^1O_2$ Production Under X-Ray of Different Irradiances 1 mL of 0.05 mg/mL M-SAO@SiO$_2$ was added in a quartz cuvette (equilibrated with air at room temperature) containing 1 µM of singlet oxygen assay. The solution was irradiated by X-ray for 5 min by a mini-X X-ray tube (Amptek Inc.), with the tube voltage set at 20 kV and currents varied from 30 to 180 µA. $^1O_2$ production efficiency was calculated by Equation 4:

$$\text{Intensity (\%)} = \frac{I - I_0}{I_0} \quad (4)$$

where $I_0$ is the fluorescence intensity at the beginning (t=0), and I is fluorescence intensity at the end of the irradiation (t=5 min).

Cell Imaging

U87-MG cells were incubated with 30 µg/mL of SAO@SiO$_2$ nanoparticle in a chamber slide for 1 h. The cells were washed three times with PBS to remove unbound nanoparticles. The nuclei were counterstained with DAPI and the slide was mounted by a glass cover slip. Images were taken on an Olympus X71 fluorescence microscope (ex/em: 360/460 nm). To monitor $^1O_2$ detection in live cells, SOSG (Molecular Probes) was used. Briefly, U87MG cells were seeded in a petri dish and grown for 24 h. The medium was then replenished with fresh medium containing 1 µM SOSG. The incubation went on for 30 min and the cells were washed with PBS to remove the excess SOSG. Subsequently, the cells were incubated with M-SAO@SiO$_2$ nanoparticles (50 μg/mL) for 4 h and then washed with PBS for three times. X-ray irradiation was applied to cells at a dose rate of 1 Sv/h for 30 min. Fluorescence images were acquired by an Olympus X71 fluorescence microscope (ex/em: 504/525 nm).

In Vitro X-PDT Using Pork as Model Tissue Obstruction

M-SAO@SiO$_2$ nanoparticles (50 μg/mL) were incubated with U87MG cells in petri dishes for 1 h at 37° C. The cells were then washed with PBS. A stack of pork slices (a total thickness of 4.5 cm) was placed between the X-ray source and the U87MG cells. Cells were exposed to X-ray for 30 min (dose rate of 1 Sv/h), and then cultured for another 24 h. Cell viability was determined by MTT assay. As a comparison, cells treated X-PDT but without pork stack were also studied.

In Vitro X-PDT

U87MG (human glioblastoma) cells were grown in Dulbecco's Modified Eagle Medium (DMEM) supplemented with 10% FBS and 100 units/mL of penicillin. The cells were maintained in a humidified, 5% carbon dioxide ($CO_2$) atmosphere at 37° C. For viability studies, $10^4$ U87MG cells were seeded in 96-well plates and cultured for 24 h. The cells were then incubated with 50 rig/ml M-SAO@SiO$_2$ (MC540 loaded SAO@SiO$_2$) nanoparticles for 1 h. SAO refers to $SrAl_2O_{4:1}$% $Eu^{2+}$; SAO@SiO$_2$ refers to a silica coated SAO nanoparticle. The particles were then washed with PBS twice, then exposed to X-ray irradiation for 30 min (1 Sv/h). Standard MTT assays were performed to evaluate the cell viability. For the controls, cells were incubated with M-SAO@SiO$_2$ nanoparticles but were not irradiated by X-ray or treated with MC540 and SAO@SiO$_2$ nanoparticles.

In Vivo X-PDT

Therapy studies began 20 days after tumor cell inoculation. Animals were randomized and treated as follows: 1) M-SAO@SiO$_2$ nanoparticles+X-ray, 2) M-SAO@SiO$_2$ nanoparticles only, 3) SAO@SiO$_2$ nanoparticles+X-ray, 4) M-SAO@SiO$_2$ nanoparticles, 5) PBS+X-ray, and 6) PBS only (n=5). Nanoparticles were injected in 50 μL PBS solutions to tumors (4.25 mg SAO/kg for both M-SAO@SiO$_2$ and SAO@SiO$_2$ nanoparticles). For groups receiving X-ray irradiation, animals were irradiated at 5 minutes after the particle injection, at a dose of 0.5 Sv (30 min). Only one dose therapy was applied to each animal. The tumor size and body weight of each animal was measured every other day. Tumors and major organs from the euthanized animals were harvested, weighted, and cryosectioned. The tissue sections were then subjected to standard H and E staining to assess treatment outcomes and side effects.

Biodistribution Study

Normal balb/c mice were injected with M-SAO@SiO$_2$ nanoparticles (4.25 mg SAO/kg, n=5). The animals were euthanized 16 days after the injection, and the major organs, such as the liver, kidney, heart, and spleen, were collected and weighed. The tissues were incubated in hot 70% nitric acid until decomposed and the solution became clear. The samples were centrifuged to remove remaining debris and the supernatants were analyzed by ICP-MS for strontium concentrations. The strontium contents in the organs were computed and expressed in ng/g tissue.

Results

The synthesized SAO nanoparticles was identified to be isostructural monoclinic $SrAl_2O_4$ (JCPDS #34-0379), doped with a trace amount of divalent state Eu (FIGS. 1A and 1B). The raw SAO displays strong photoluminescence and XEOL, which emission spectra are comparable (FIGS. 1C and 1D). Both types of luminescence are attributable to $4f^6 5d^1 \rightarrow 4f^7$ transition of $Eu^{2+}$ ions, in particular the preferential orientation of the $Eu^{2+}$5d orbital along the host cation chain in the lattice.

Figures 2A, 2B, 2C, 2D:
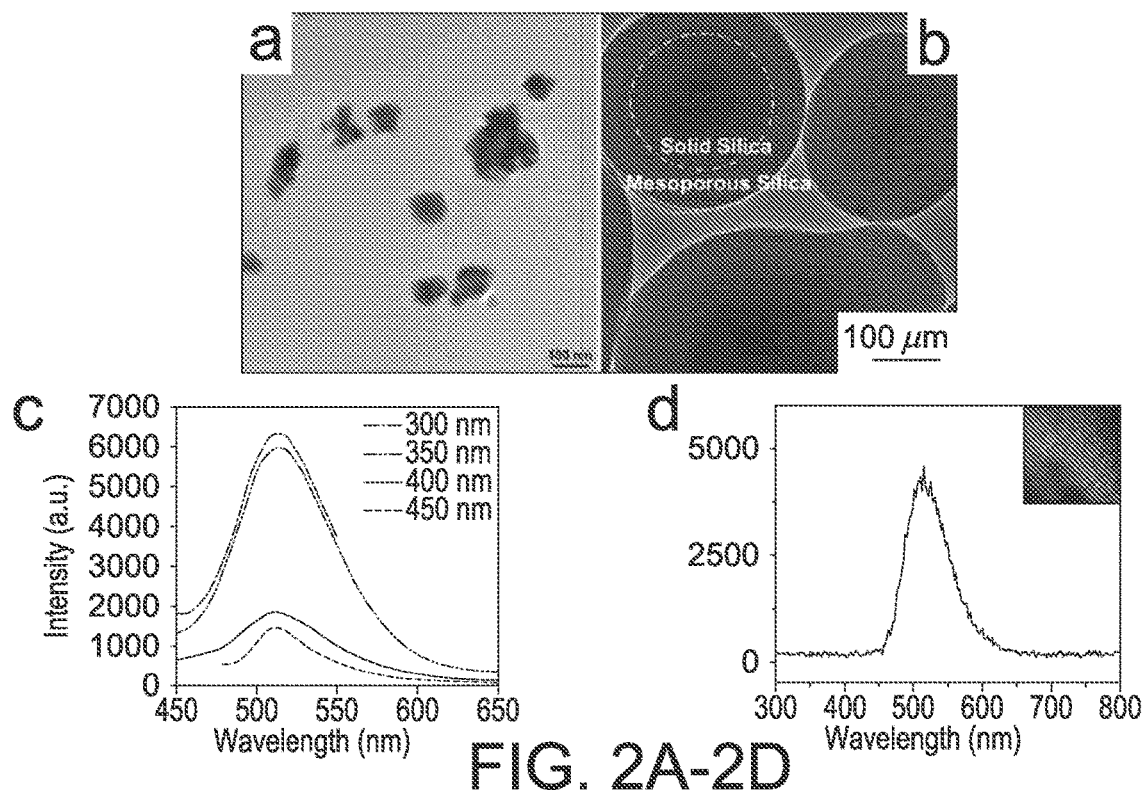
FIGS. 2A-2D show the morphology and optical properties of SAO@SiO$_2$ nanoparticles.
Figures 3A, 3B, 3C, 3D, 3E, 3F, 3G:
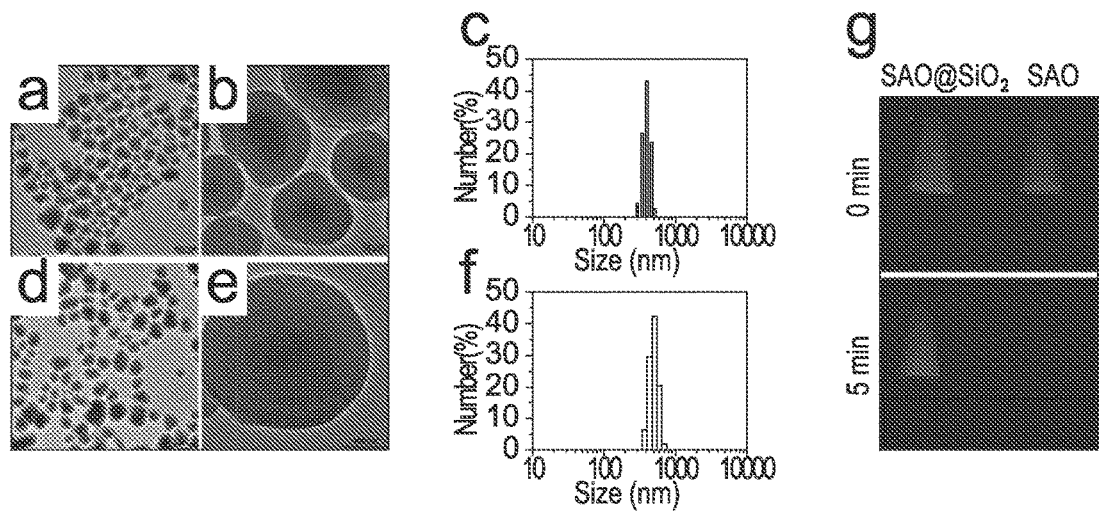
FIGS. 3A-3G shows the size, size distribution, and stability of silica coated SAO nanoparticles.
Figures 4A, 4B, 4C:
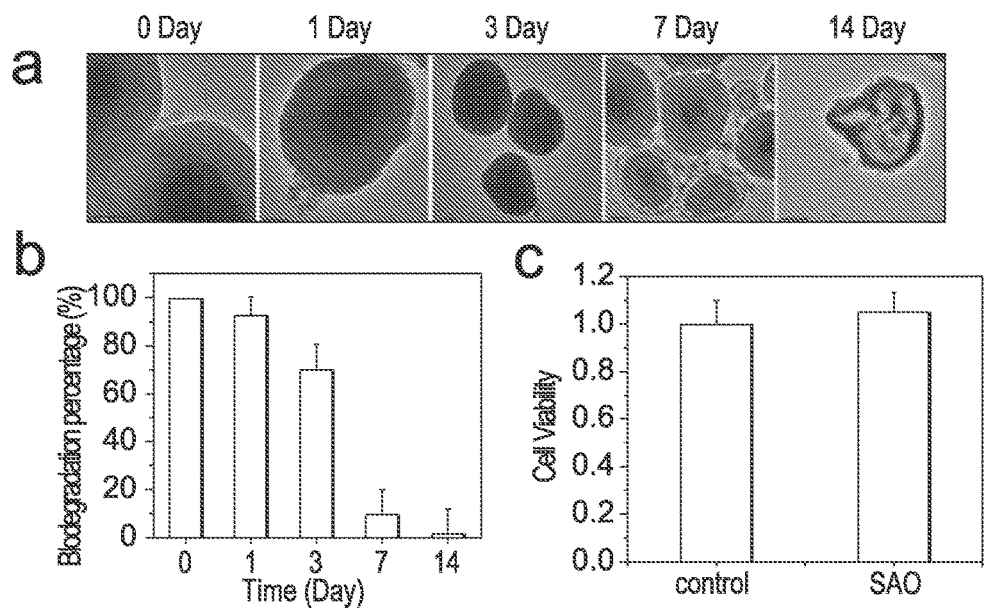
FIGS. 4A-4C show the degradation of SAO nanoparticles.
Figures 5A, 5B, 5C:
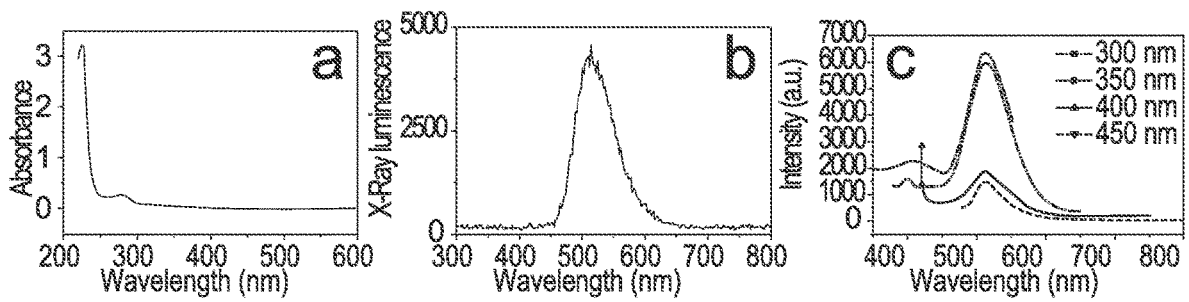
FIGS. 5A-5C show the optical properties of as-synthesized SAO.

The dimensions of the synthesized SAO particles were reduced by mechanically groundling, followed by sedimentation, filtration and centrifugation, to yield c.a. 150 nm nanoparticles (FIG. 2A). The SAO nanoparticles were then coated with silica, to contain one inner solid layer and one outer mesoporous layer (FIG. 2B, FIGS. 3A-3F). Each of the two silica layers plays a distinctive role in the nanosystem. The inner, solid silica coating functions as a protection shell that prevents the SAO core from contacts with the surroundings (FIGS. 4A-4C). The role of protection is important because SAO is highly hydrolytic; naked SAO nanoparticles can completely degraded in 5 min when directly exposed to aqueous solutions (FIG. 3G). The solid silica coating can extend the lifetime of the SAO nanoparticles in aqueous solutions up to 7 days (FIGS. 4A and 4B), and/or a duration that suffices for therapy purposes. The outer, mesoporous silica coating provides a docking place for small molecules. Notably, for the mesoporous coating, both aminopropyltriethoxysilane (APTES) and tetraethyl orthosilicate (TEOS) for silane precursors were used. The resulting silica coated SAO nanoparticles (SAO@SiO$_2$ nanoparticles), thus present multiple amine groups on the surface and are slightly positively charged.

Figures 6A, 6B, 6C, 6D, 6E:
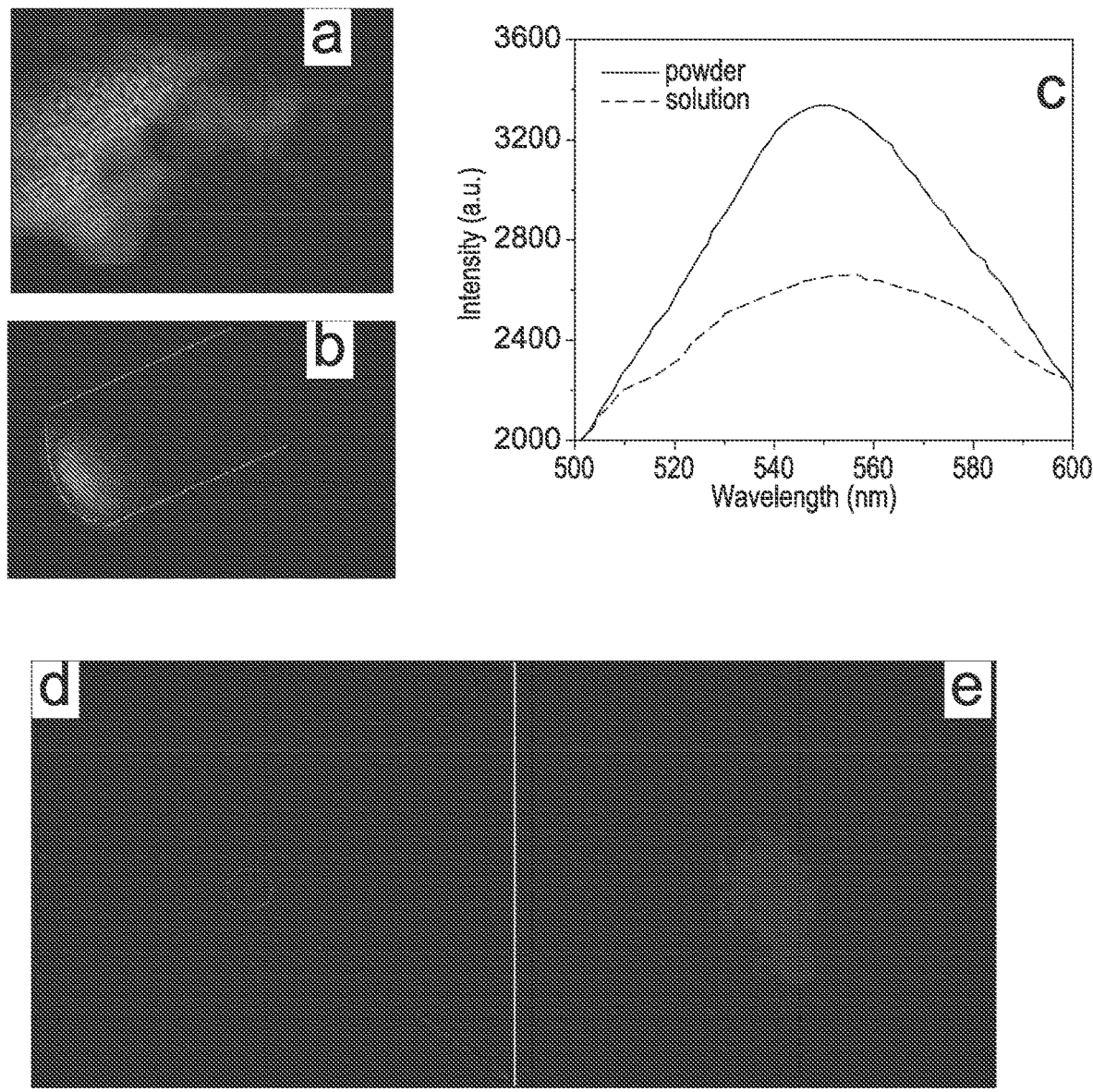
FIGS. 6A-6E show X-ray excited optical luminescence of SAO@SiO$_2$ nanoparticles.

SAO@SiO$_2$ nanoparticles maintain the strong photoluminescence and XEOL of SAO. FIGS. 2C and 2D show emission spectra of SAO@SiO$_2$ nanoparticles under irradiation by UV/Vis light and X-ray, respectively. Similar to the bulk material, both types of emission was found in the green spectrum region, peaking around ~520 nm (FIGS. 2C and 2D, FIGS. 5A-5C). The emission was visualized on a small animal Maestro imaging system (FIG. 6A-6C). The emission can also be was visualized by the naked eyes (FIG. 6D-6E).

Figures 7A, 7B:
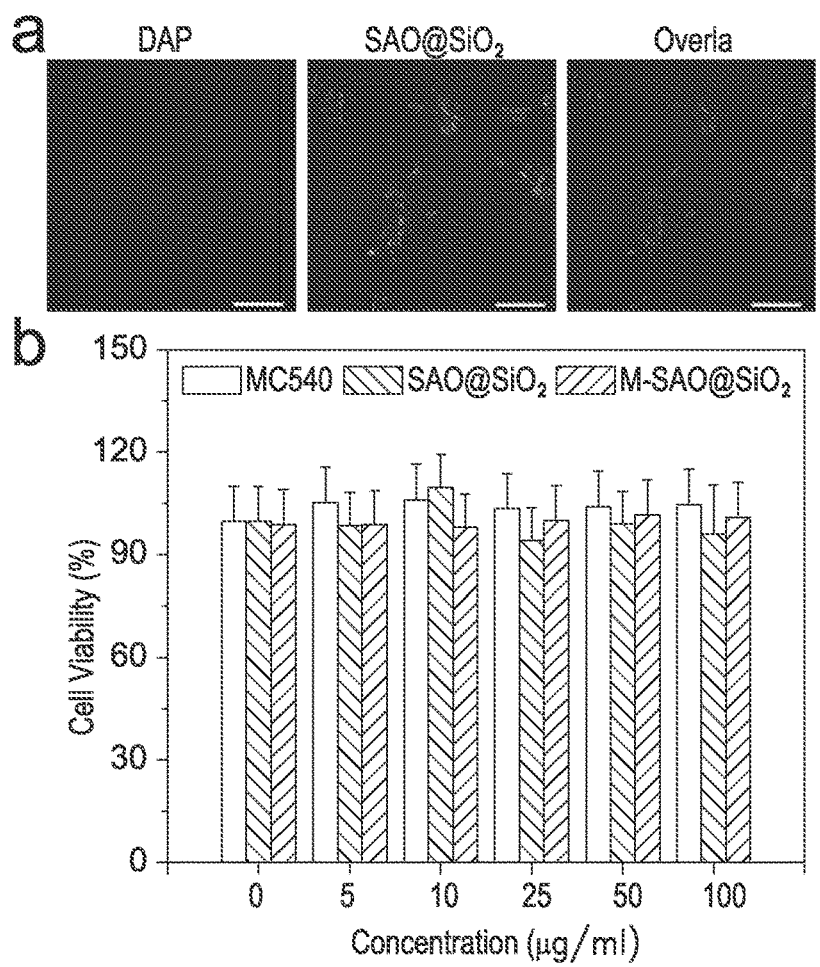
FIG. 7A shows the uptake of SAO@SiO$_2$ nanoparticles by U87MG cells (scale bars: 50 μm). Blue, DAPI (ex/em: 360/460 nm). Green, SAO@SiO$_2$ nanoparticles (ex/em: 360/520 nm).
FIG. 7B shows MTT assay results with MC540, SAO@SiO$_2$, and M-SAO@SiO$_2$ nanoparticles after 24 h incubation.

Cellular uptake of the nanoparticles was investigated with U87MG (human glioblastoma) cells. After incubation with SAO@SiO$_2$ nanoparticles (50 rig/mL) for 1 h, the cells were washed with PBS and imaged under a fluorescence microscope. The images are shown in FIG. 7A. A 360-nm light was used to excite the SAO@SiO$_2$ nanoparticles. Green photoluminescence was observed in all the cells within the scope of the radiation. The green photoluminescence was distributed across the cytoplasm but not the nuclei. These results show that SAO@SiO$_2$ nanoparticles were internalized by cells through endocytosis, a process that may have been facilitated by electrostatic interactions between the particles and the cell membranes (FIG. 7A).

Using MTT (3-(4,5-dimethylthiazol-2-yl)-2,5-diphenyltetrazolium bromide) assays, the cytotoxicity of SAO@SiO$_2$ nanoparticles was investigated. No significant viability drop even at high particle concentrations (up to 100 μg/mL, FIG. 7B), suggesting good biocompatibility. However, MTT assays are only viable to assess short-term cytotoxicity (e.g. within 24 or 72 h) when most of the nanoparticles are still intact. As mentioned above, SAO is highly hydrolytic, and despite the presence of the SiO$_2$ coating, the nanoparticle core can be degraded in a physical environment after one week. The released constituent ions, including $Sr^{2+}$, $Al(OH)_4$ (the primary form at neutral pH), and $Eu^{2+}$, may affect cell viability differently. To investigate, in a separate study, SAO nanoparticles was incubated in water for 30 min to decompose SAO, and then the hydrolytes was used for toxicity assessments. Again, no significant drop of viability was observed, confirming minimal toxicity of the nanoparticles even in the long run (FIG. 4C). All the constituent ions used in the nanoparticles have relatively low toxicity profiles. $Sr^{2+}$ and $Al^{3+}$ have been used in clinical medicines for applications such as postmenopausal osteoporosis, antacid, and bone implants. $Eu^{2+}$ is also relatively low-toxic compared to other heavy metals.

Figure 8:
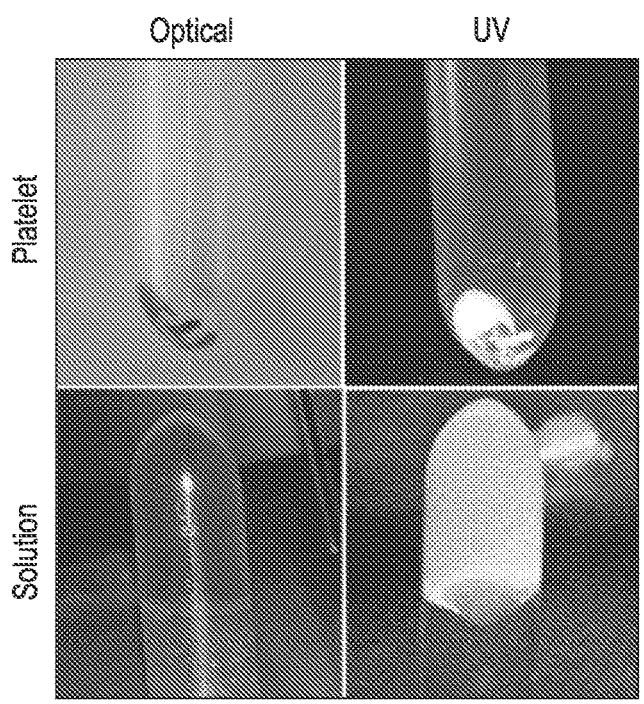
FIG. 8 shows photographs of M-SAO@SiO$_2$ in powder (upper panel) and solution (lower panel) under day light or irradiated in the dark by 360-nm UV light.

The mesoporous coating allows easy loading of small molecules. Through overnight incubation, MC540 at a rate of 15 wt % was loaded onto $SAO@SiO_2$ nanoparticles. Despite the heavy loading, the resulting MC540-loaded $SAO@SiO_2$ nanoparticles, or $M-SAO@SiO_2$ nanoparticles, remained highly stable in aqueous solutions as shown in FIG. 8.

Figures 9A, 9B, 9C, 9D, 9E:
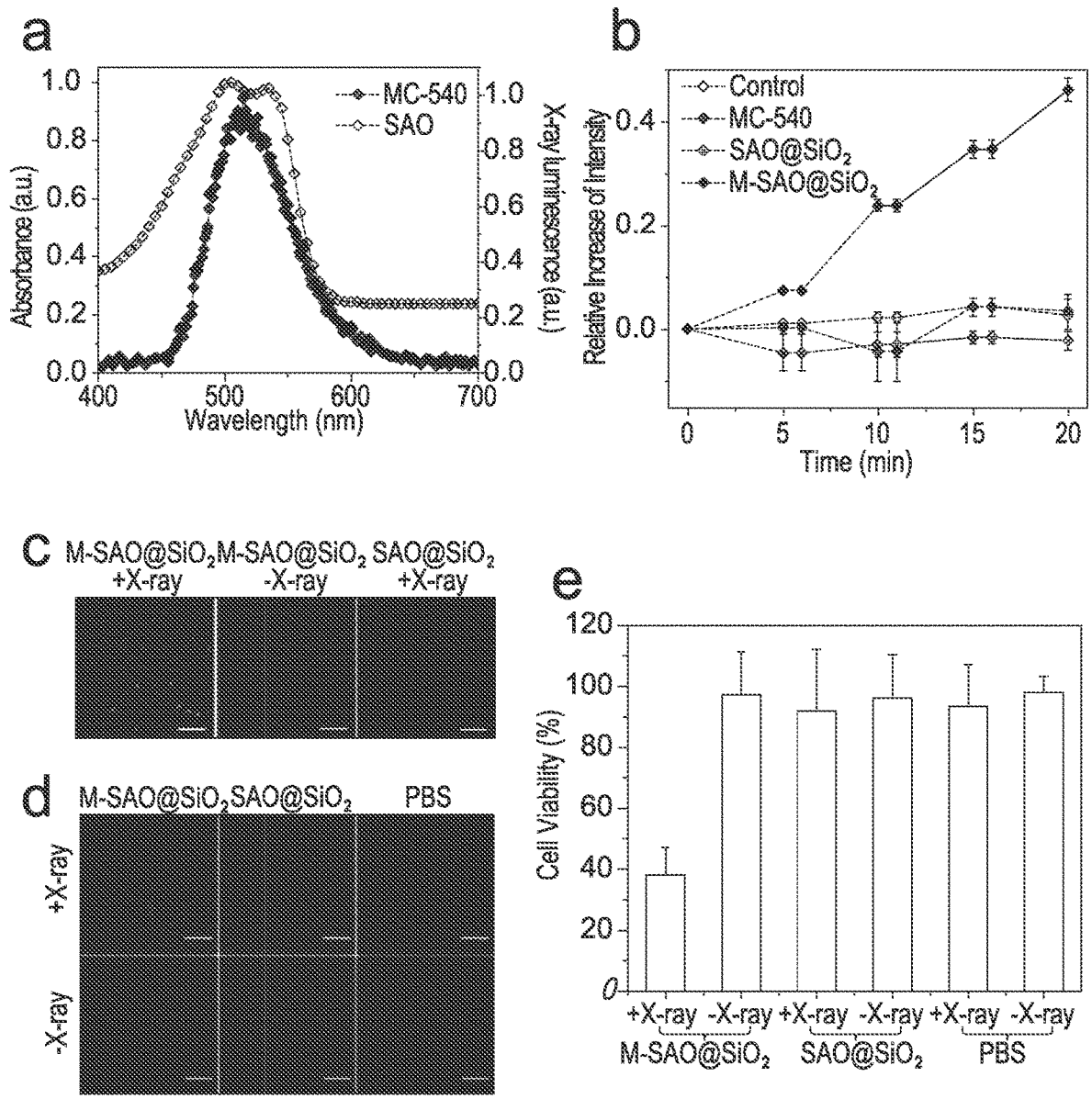
FIGS. 9A-9E show the $^1O_2$ production by X-PDT and induced cytotoxicity.

There is a significant overlap between the XEOL of SAO and the excitation wavelength of MC540 (FIG. 9A). Therefore, the ability of $M-SAO@SiO_2$ nanoparticles irradiated by X-ray to relay energy in the form of visible photons to MC540 and as a result, producing $^1O_2$ was investigated. A common $^1O_2$ indicator, singlet oxygen sensor green (SOSG, Invitrogen) was used to investigate this effect. SOSG is a fluorescent compound which undergoes a structural change in the presence of $^1O_2$. The process is accompanied by an increase of fluorescence (ex/em: 504/525 nm). Therefore, by measuring the fluorescence change, the $^1O_2$ generation in solutions or cells can be monitored. Using SOSG, $^1O_2$ generation with a $M-SAO@SiO_2$ nanoparticle solution (50 μg/mL) under X-ray irradiation was studied (1 Sv/h, FIG. 9B). Compared to the background, the intensity of 525 nm fluorescence was increased by 8, 25, 35, and 45% after 5, 10, 15, and 20 min X-ray irradiation, respectively (FIG. 9B). Meanwhile, no significant signal increase was observed during the intermissions of X-ray irradiations (FIG. 9B). Similar studies were performed with solutions of MC-540, SAO nanoparticles, and PBS, all of which showed minimal increase in fluorescence, either with or without X-ray (FIG. 9B). These data showed that $^1O_2$ can, and only can be produced when all the three components—MC-540, SAO, and X-ray—are in presence, corroborating our hypothesis that $^1O_2$ production is a result of SAO-mediated energy transfer.

Figure 10:
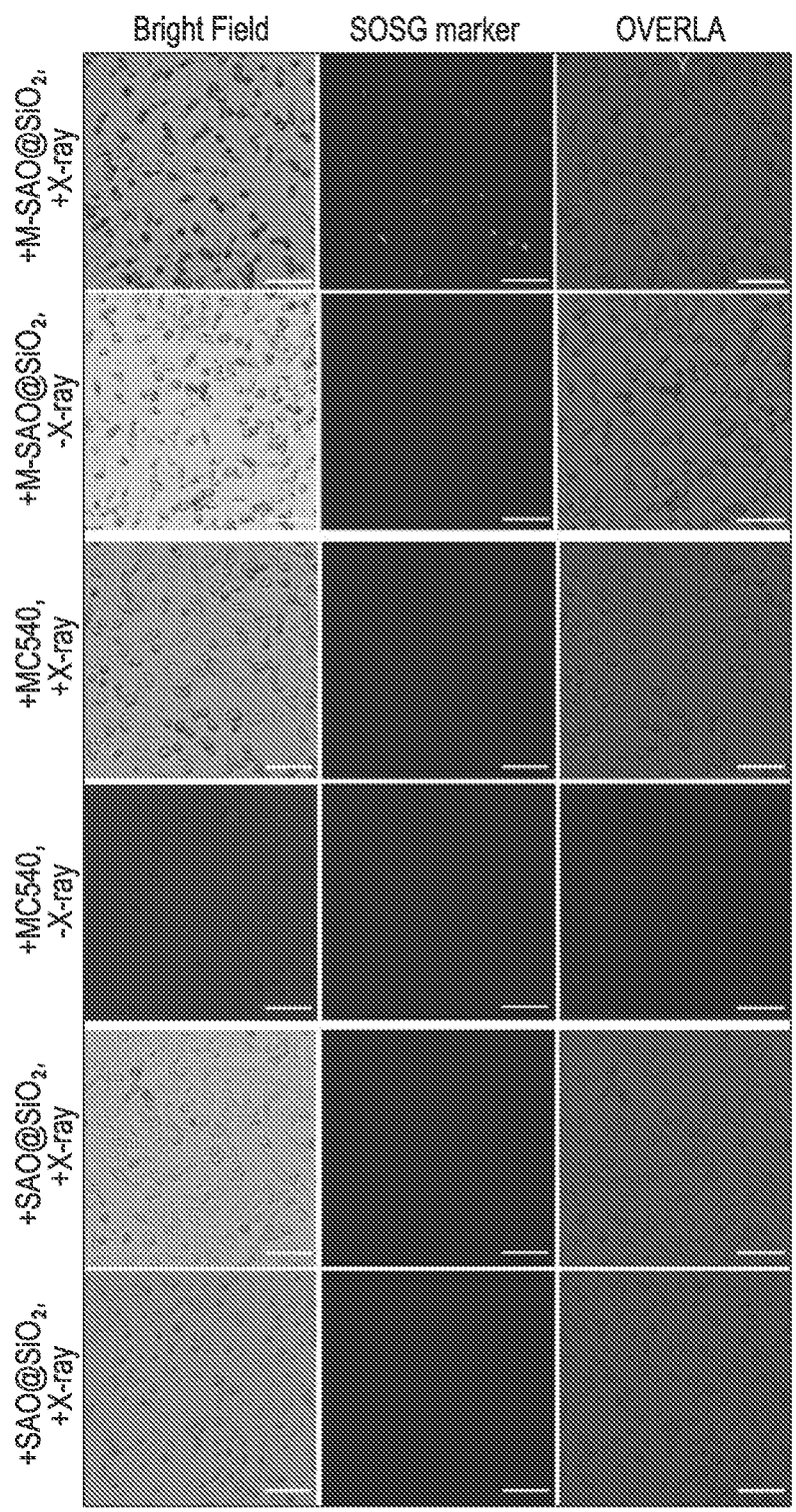
FIG. 10 shows $^1O_2$ production in cells. U87MG cells were incubated with M-SAO@SiO$_2$ nanoparticles, SAO@SiO$_2$ nanoparticles, or MC540, with and without subsequent X-ray irradiation. SOSG was used as a $^1O_2$ indicator. Enhanced fluorescence (ex/em: 504/525 nm) was only observed with cells treated with combination of M-SAO@SiO$_2$ nanoparticle and X-ray. Scale bars, 100 μm.

The $^1O_2$ production with U87MG cells, again using SOSG as an indicator was also investigated. There was significant enhancement of 525 nm fluorescence observed in X-ray irradiated cells incubated with $M-SAO@SiO_2$ nanoparticles compared to cells that were not irradiated (FIG. 9C and FIG. 10). Quantification of the fluorescence readings from each group (Image J, National Institutes of Health), showed that a 410±29% enhancement in the fluorescence of the X-PDT treated cells was obtained. The cells treated with $M-SAO@SiO_2$ only (without X-ray irradiation) or $SAO@SiO_2$ nanoparticles (with or without X-ray irradiation) showed merely marginal increase of fluorescence. This confirms that a combination of X-ray, MC540, and SAO is required to generate $^1O_2$.

Figures 11A, 11B:
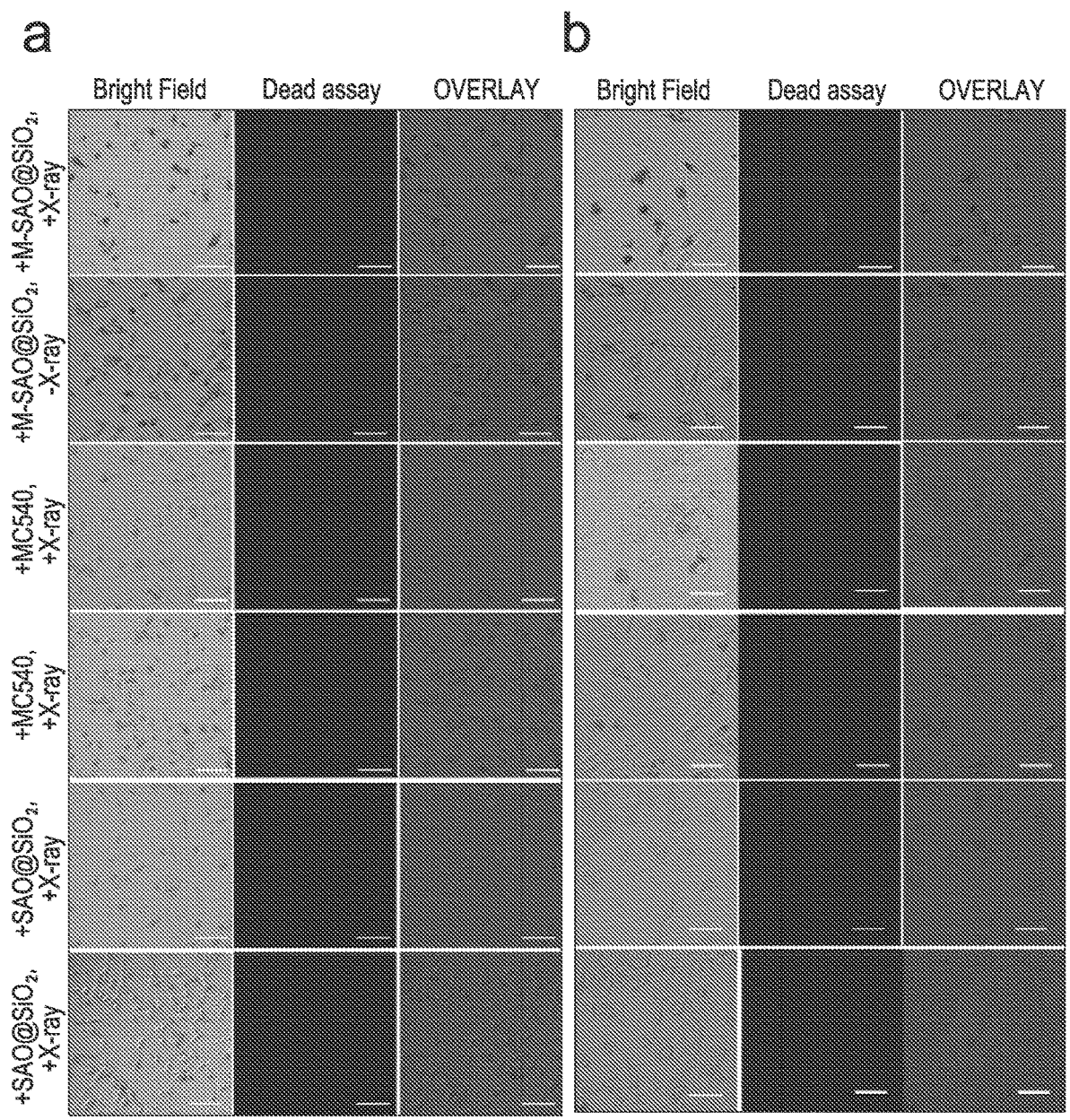
FIGS. 11A-11B show the cytotoxicity at low (FIG. 11A) and high (FIG. 11B) magnification, caused by X-PDT studied by ethidium homodimer-1 assay; M-SAO@SiO$_2$ nanoparticles (0.05 mg/mL) were incubated with U87MG cells for 1 h before X-ray irradiation. Consistent with the observations in FIG. 10, toxicity was only found with cells treated with the M-SAO@SiO$_2$ nanoparticle and X-ray combination. Ex/em: 504/525 nm. Scale bars, 100 μm.
Figures 12A, 12B:
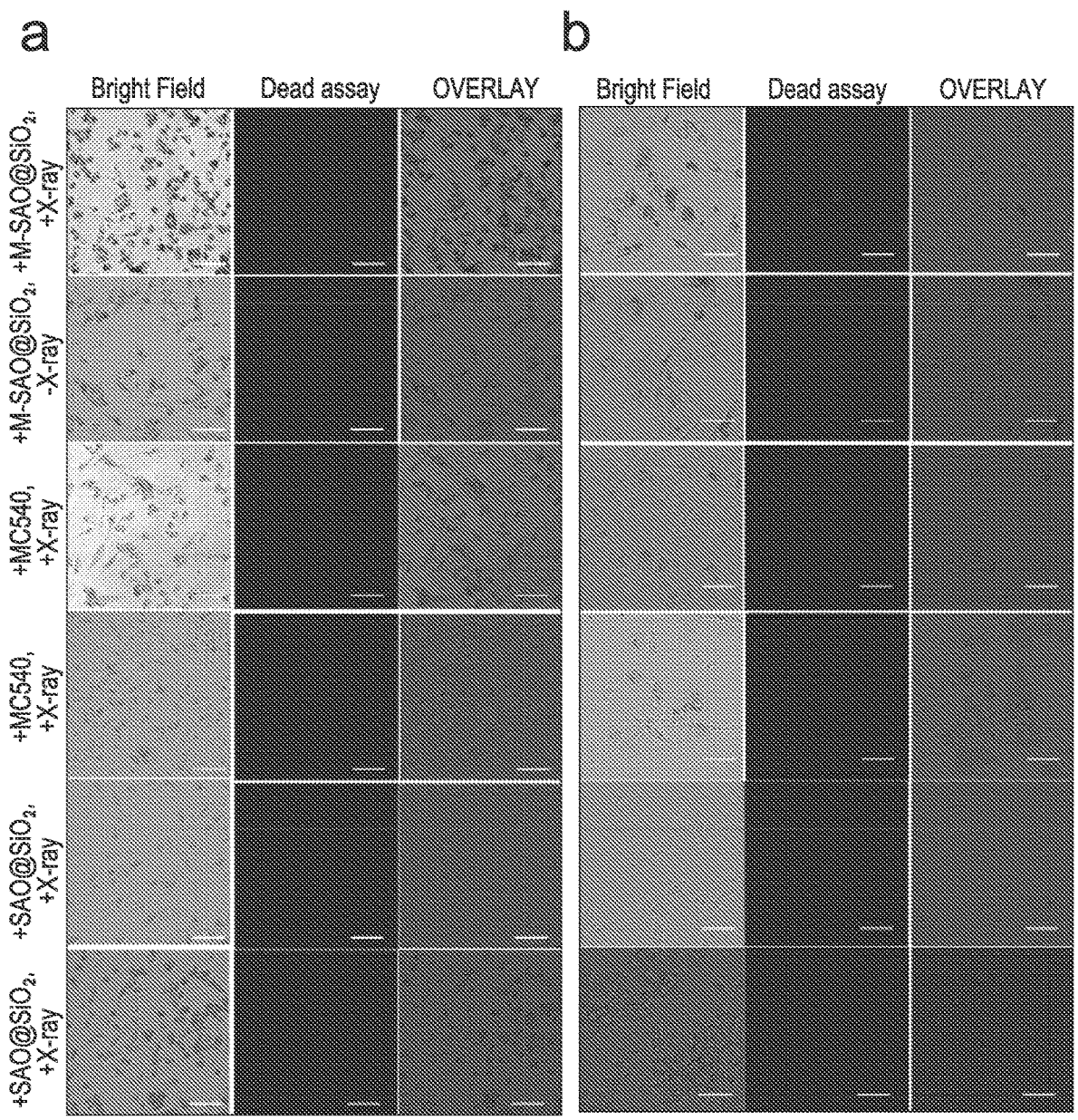
FIGS. 12A-12B show the results from cytotoxicity studies at low (FIG. 12A) and high (FIG. 12B) magnification, caused by X-PDT using the ethidium homodimer-1 assay; M-SAO@SiO$_2$ nanoparticles (0.05 mg/mL) were incubated with U87MG cells for 24 h before X-ray irradiation. Ex/em: 530/635 nm. Scale bars, 50 μm.

The $^1O_2$ generated translates to toxicity to cells. FIG. 9D shows a cytotoxicity assay where ethidium homodimer-1 was used to mark dead cells with red fluorescence (ex/em: 517/617 nm). Low red fluorescence intensity was observed with U87MG cells treated with X-ray alone or $M-SAO@SiO_2$ nanoparticles in the absence of X-ray irradiation (FIG. 9D). A significant increase of red fluorescence was observed within cells treated with $M-SAO@SiO_2$ nanoparticles and irradiated (FIG. 9D). In addition to the increased red fluorescence obtained, the cell morphology was also changed (FIGS. 11 and 12). The result was further confirmed by MTT assays, which found a viability drop by 62% with X-PDT-treated cells but little toxicity in all the control groups (FIG. 3E).

In vivo therapy studies were conducted in murine subcutaneous tumor models. Briefly, 30 U87MG tumor bearing mice were randomized to receive the following treatments (n=5): 1) $M-SAO@SiO_2$ nanoparticles+X-ray, 2) $M-SAO@SiO_2$ nanoparticles only, 3) $SAO@SiO_2$ nanoparticles+X-ray, 4) $M-SAO@SiO_2$ nanoparticles only, 5) PBS+X-ray, and 6) PBS. For Groups 1-4, $SAO@SiO_2$ or $M-SAO@SiO_2$ nanoparticles were intratumorally injected to the animals (4.25 mg SAO/kg, in 50 μL of PBS solution, 1.7 mg SAO/ml, single dose). For groups 5 and 6, 50 μL of PBS was intratumorally injected. For animals receiving X-ray (Group 1, 3, and 5), the irradiation was applied to tumors for 30 min at a rate of 1 Sv/h after particle injection. Notably, this irradiation dose is far below those used in clinical radiation therapy (e.g. 60-80 Gy for solid epithelial tumors, 5 Gy/fraction).

Figures 13A, 13B, 13C, 13D:
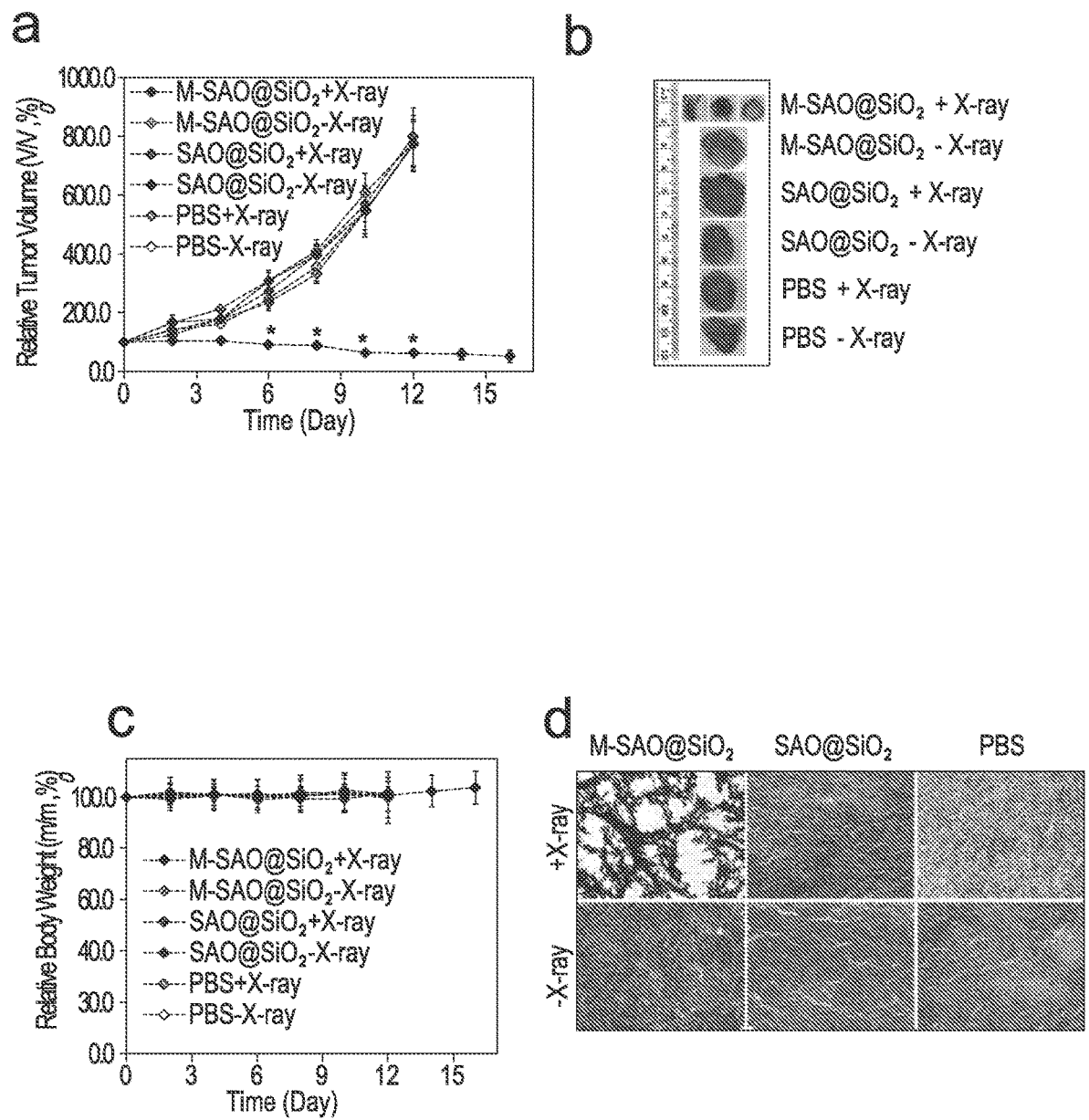
FIGS. 13A-13D show the results from X-PDT in in vivo tumor treatments.
Figure 14:
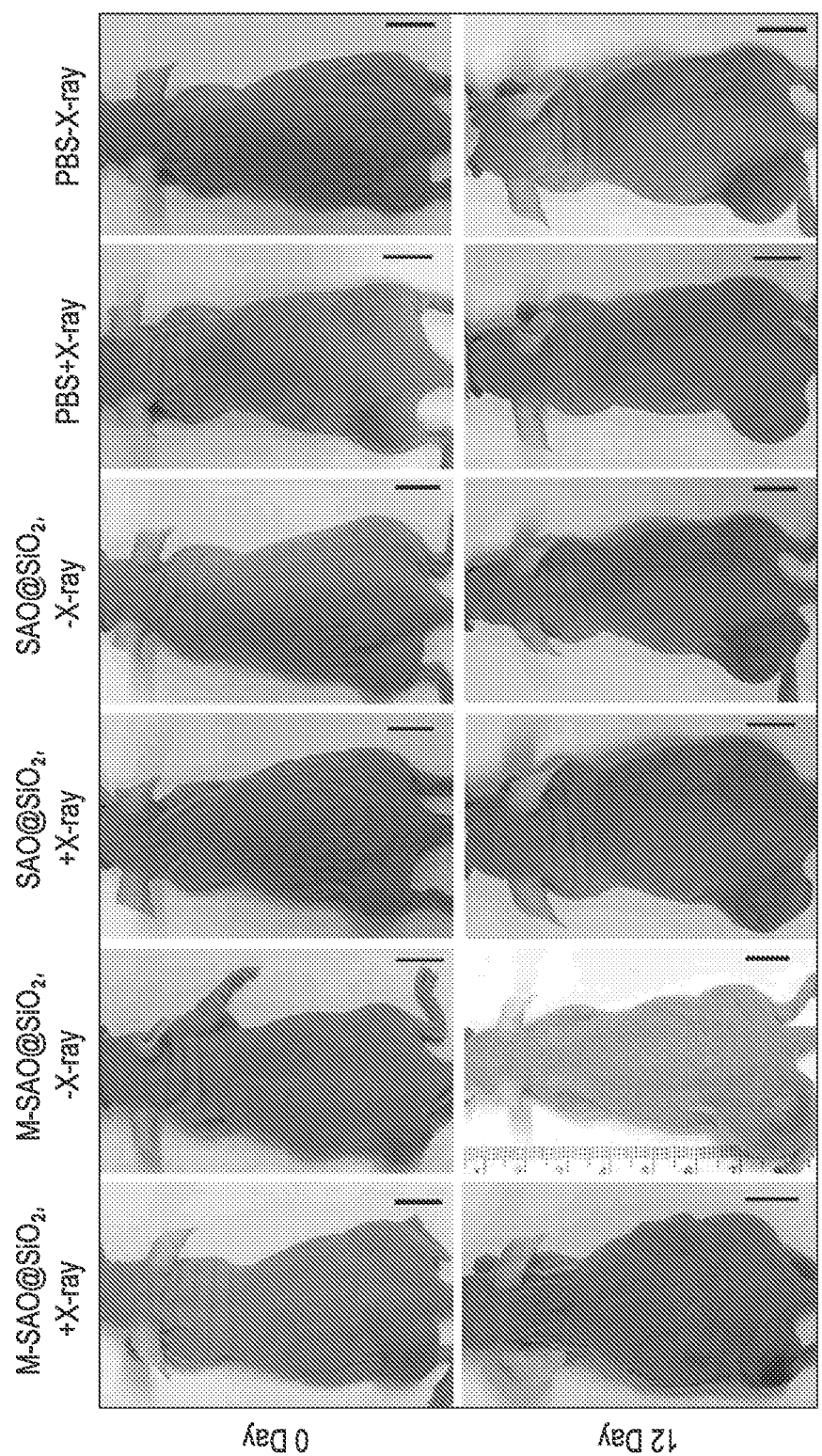
FIG. 14 shows representative photographs of mice from Groups 1-6 on day 12 (scale bar: 1 cm).
Figure 15:
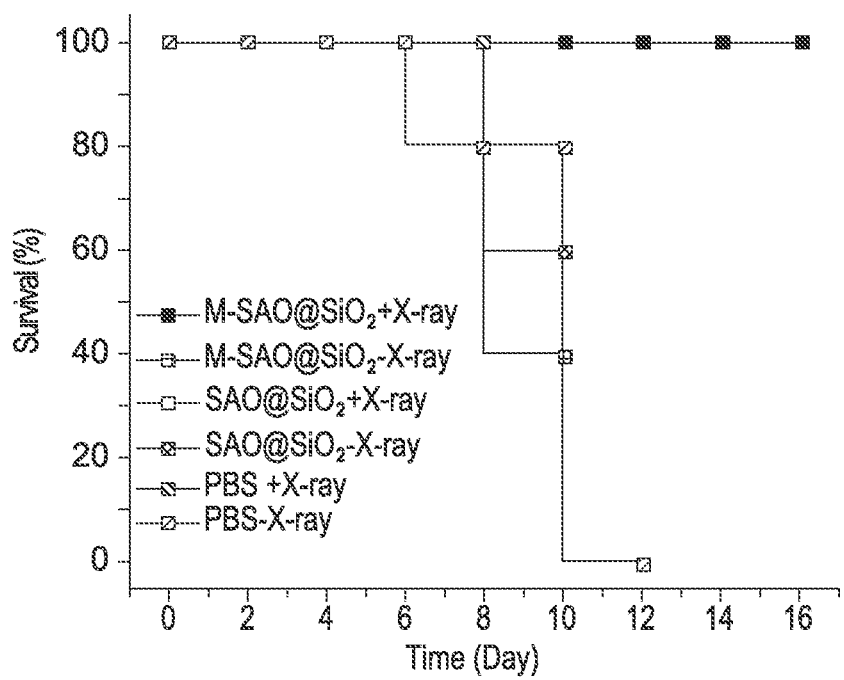
FIG. 15 shows the survival curves of animals for Group 1-6.

Relative changes of tumor volumes ($V/V_0$) were graphed in FIGS. 13A-13D. For Group 1, tumor growth was immediately arrested after the treatment, followed by significant tumor shrinkage starting from day 6. On day 12, the average tumor volume was reduced to 60.2±6.9% (FIG. 13A). On day 16, three of the five animals showed almost impalpable tumors, leaving only thin scabs at the original tumor sites (FIG. 13B and FIG. 14). All the animals in Group 1 were healthy through the whole study (FIG. 13C). On the contrary, all the animals in the control groups showed rapid and comparable tumor growth (FIG. 13A and FIG. 14). On day 12, tumor volumes were increased by 768.0±87.0%, 797.4±98.6%, 776.9±91.9%, 767.4±80.8%, and 773.1±80.4% for Group 2-6, respectively (FIGS. 13A and 13B). By day 14, all the animals in the control groups had either died or met at least one humane end point (FIG. 15).

Figures 16A, 16B:
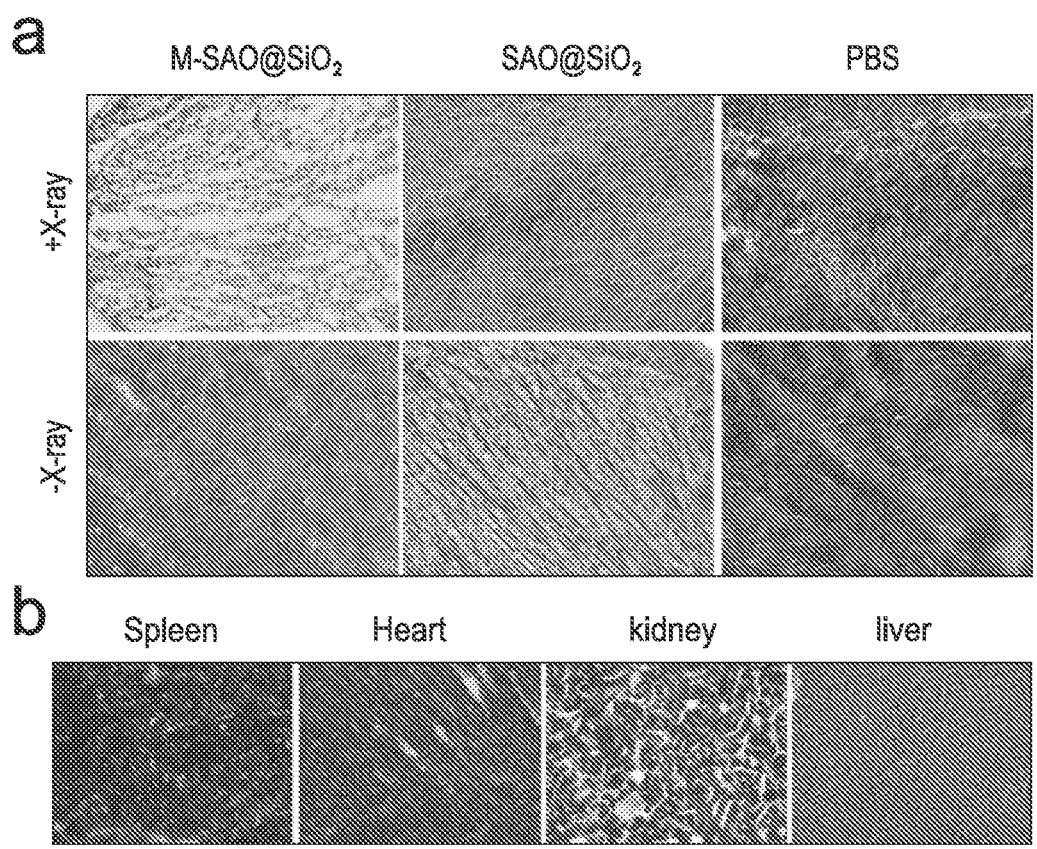
FIG. 16A-16B show H and E staining with tumor and normal tissue samples.

Post-mortem H and E staining showed densely packed neoplastic cells in tumors from the control groups (FIG. 13D and FIG. 16A). The treatment group showed significantly impacted tumor architectures with significantly reduced cell density (FIG. 9D and FIG. 16), with many regions void of viable cells. There was no detectable impact to the normal tissues, such as the heart, liver, spleen, kidneys, and skin (FIG. 16B). This is due to the high selectivity of the X-PDT treatment, and also, the low toxicity and high biodegradability of SAO nanoparticles.

Figures 17A, 17B, 17C:
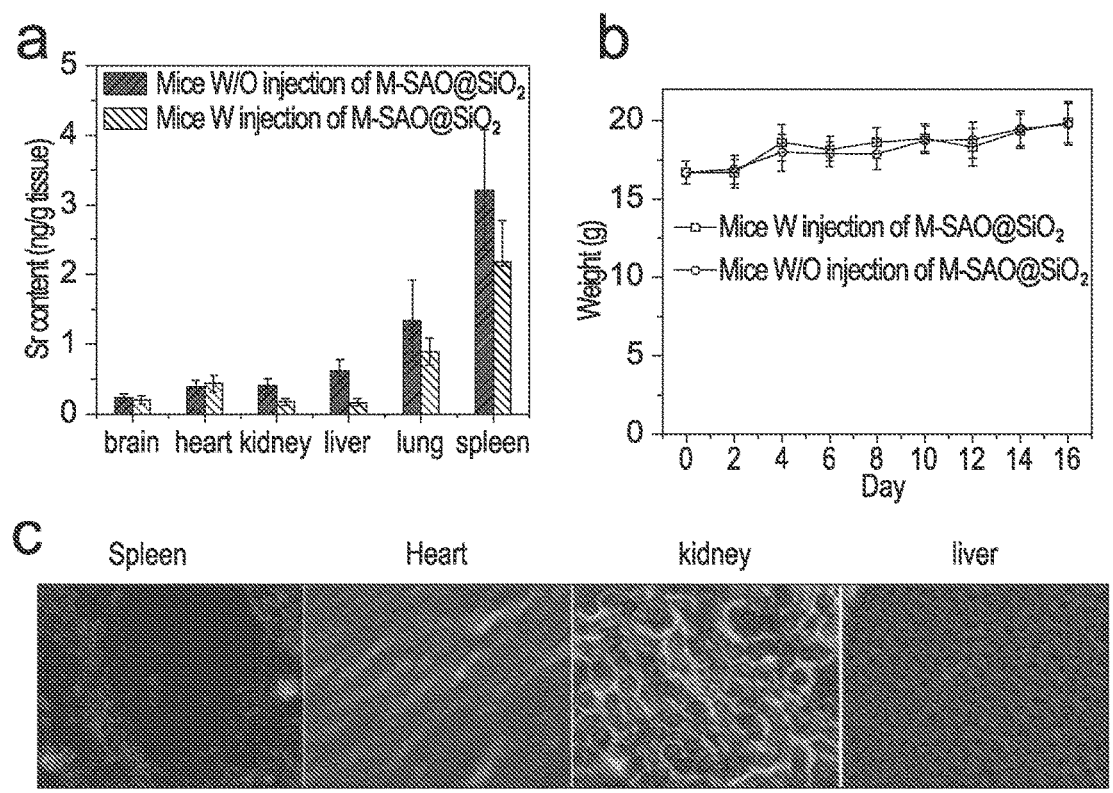
FIGS. 17A-17C show the in vivo biodistribution and toxicity studies.

The excretion of SAO particles was assessed by intravenously injecting $M-SAO@SiO_2$ nanoparticles to normal balb/c mice. On day 16, the animals were sacrificed and the remaining Sr contents were evaluated in different organs by inductively coupled plasma mass spectrometry (ICP-MS) analysis. For all the organs analyzed, Sr contents that were comparable to the background, confirming the efficient clearance of the particles were found (FIG. 17A). All the injected animals were healthy throughout the whole study (FIG. 17B), and there was no sign of toxicity to the normal tissues (FIG. 17C).

Figure 18:
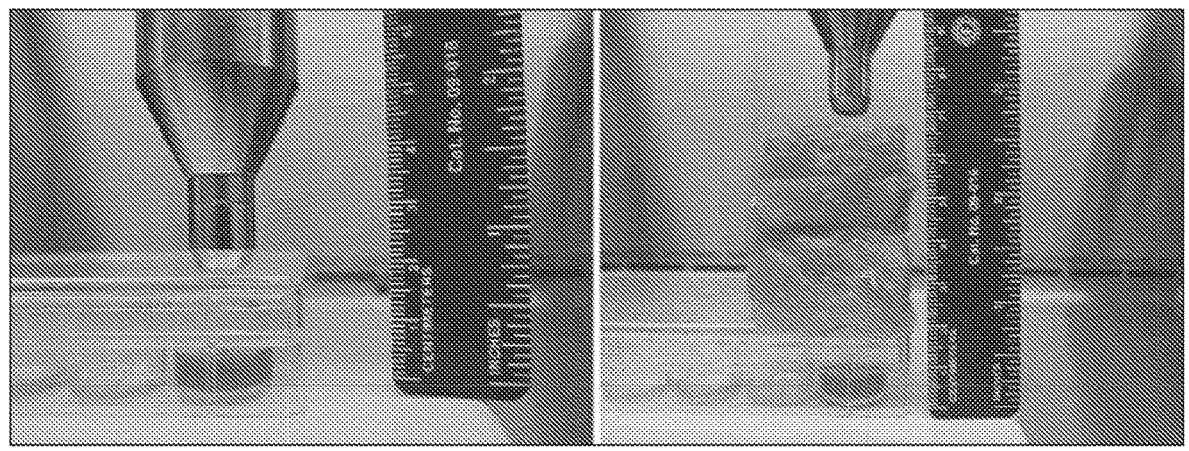
FIG. 18 shows photographs of the experimental setup for assessing in vitro toxicity induced by X-PDT without (left) and with (right) pork.
Figure 19A:
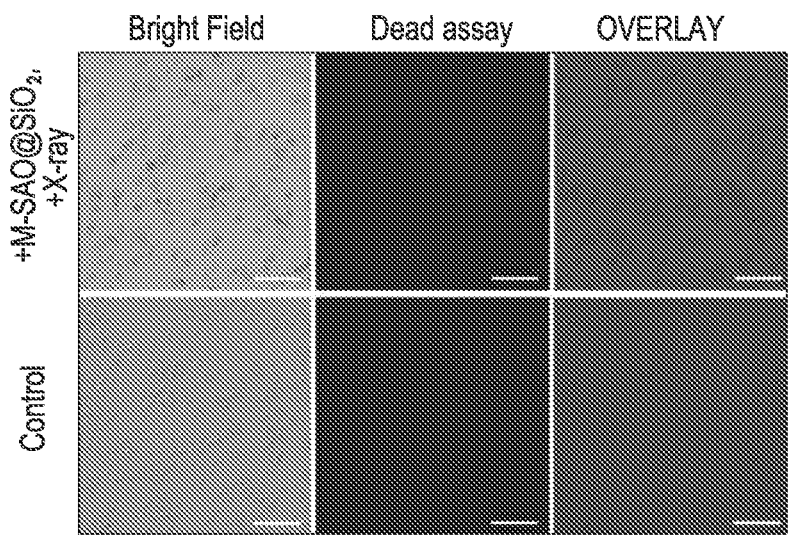
FIG. 19A-19B show in vitro cytotoxicity by X-PDT, with pork blocked between the X-ray source and the cells.
Figure 19B:
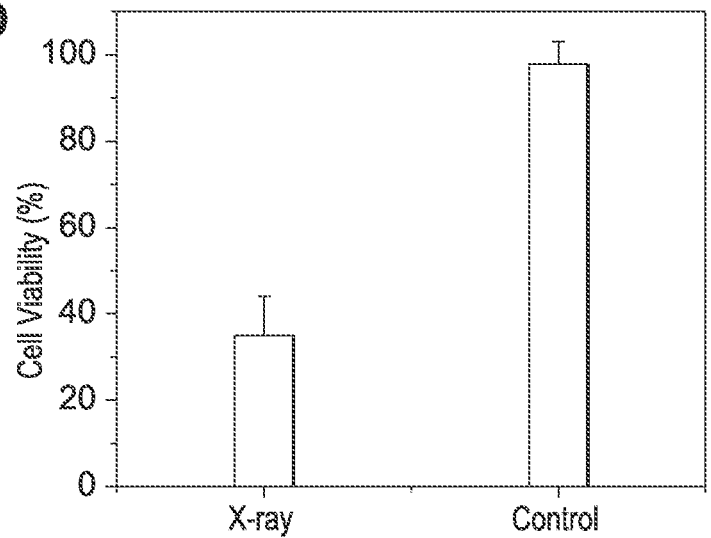
Figure 20:
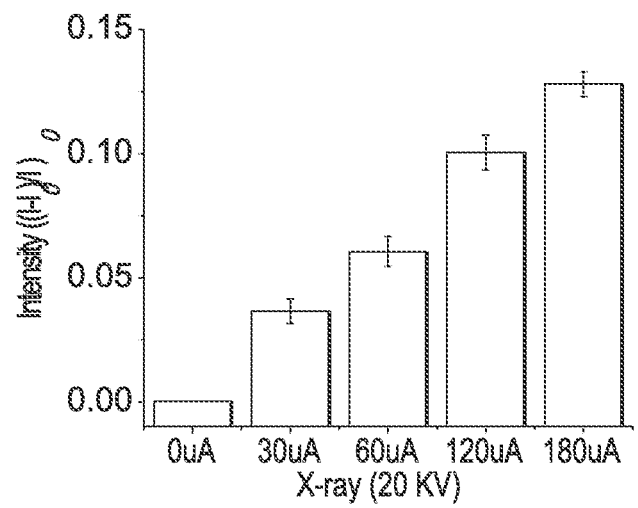
FIG. 20 shows a comparison of $^1O_2$ production with the X-ray generator operating at different currents. The voltage was fixed at 20 kV.

The efficacy of the method was supported by a cytotoxicity study where U87MG cells were treated with $M-SAO@SiO_2$-mediated X-PDT, but with 4.5-cm thick pork positioned between the X-ray source and cells (FIG. 18). There was no significant difference in viability drop relative to the cells receiving X-PDT with direct X-ray irradiation (35±9% vs. 38±9% for cells treated with and without pork, respectively, P<0.05, FIGS. 19A-B). This shows the independence of X-PDT to tissue depth, a quality that is missing by conventional PDT.

Figures 22A, 22B, 22C:
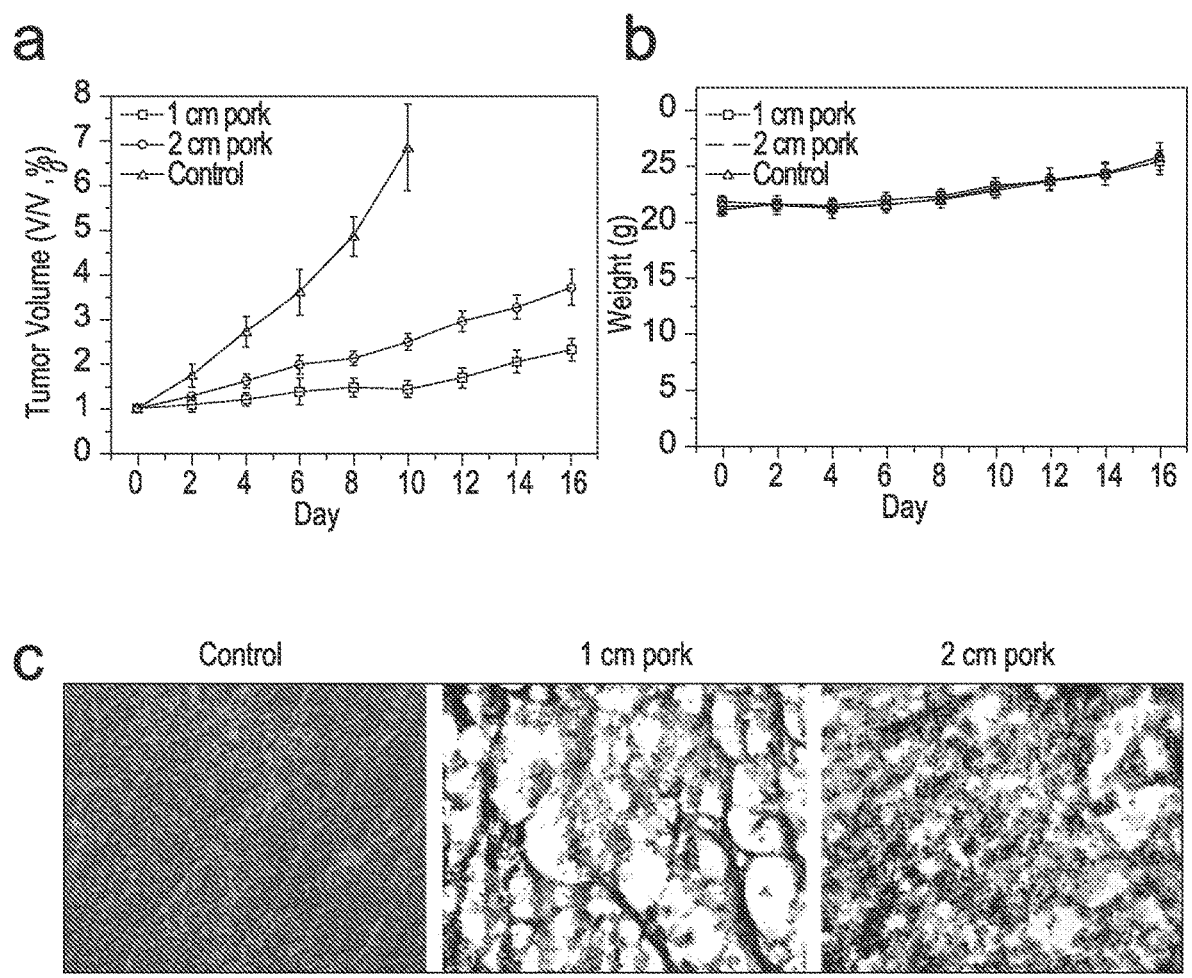
FIGS. 22A-22C show the efficacy of the X-PDT technology to treat tumors located deep under the skin. SAO nanoparticles were intratumorally injected to U87MG xenograft tumor models. X-ray (0.5 Gy) was applied to tumors over a narrow beam. Pork of 1 or 2 cm in thickness was used as tissue mimics to lie on top of tumors. Despite the pork as X-ray blockes, the X-PDT can effciently suppress tumor growth (FIG. 22A). The treatment caused no weight loss of the animals (FIG. 22B). The efficacy of the treatment was confirmed by H and E staining on tumor tissues (FIG. 22C), finding extensively destructed tumor structures in the treatment groups.

SAO nanoparticles were also intratumorally injected to U87MG xenograft tumor models. X-ray (0.5 Gy) was applied to tumors over a narrow beam. Pork of 1 or 2 cm in thickness was used as tissue mimics to lie on top of tumors. Despite the pork as X-ray blockes, the X-PDT can efficiently suppress tumor growth (FIG. 22A). The treatment caused no weight loss of the animals (FIG. 22B). The efficacy of the treatment was confirmed by H and E staining on tumor tissues (FIG. 22C), finding extensively destructed tumor structures in the treatment groups.

SAO nanoscintillators were used for X-ray-to-visible conversion. SAO is an inorganic luminescent material. In addition to its excellent optical properties, there are at least two more advantages of SAO for the current application. First, SAO forms an excellent energy pair with MC540, ensuring efficient intra-particle energy transfer that leads to $^1O_2$ production. Based on the reported $E_{gap}$ of SAO, it is calculated that the X-ray-to-visible conversion efficiency is ~77,000 optical photons per MeV, which accounts for 18.4% energy conversion efficiency (details of the calculation are described above). For M-SAO@SiO$_2$ nanoparticles, it was characterized that the efficiency of visible photons to activate MC540 is 66.7% (calculation described above). This gives rise to an overall $^1O_2$ production efficiency of 12.3%, which is high. Second, SAO is highly hydrolytic and its hydrolytes have low toxicity. With silica as a semi-stable protection shell, the SAO core maintains for a time span sufficient for the therapy, and is then reduced to constituent ions that are readily excretable. This property minimizes any long-term toxicity to the host, which is a common issue in nanoparticle-based imaging and therapy.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A photodynamic therapy system, comprising:
   (a) a strontium aluminum oxide nanoparticle of formula $Sr_aAl_bO_c$, where a, b and c are integers from 1 to 30, doped with $Eu^{2+}$, $Dy^{3+}$, $Nd^{3+}$, or combinations thereof that emits electromagnetic radiation having a first wavelength when irradiated with electromagnetic radiation having a second wavelength and wherein nanoparticle is from 5 nm to 5000 nm;
   (b) a photosensitizer which absorbs electromagnetic radiation of said first wavelength;
   (c) a first shell comprising a biocompatible mesoporous silica that forms a coating on the surface of the nanoparticle; and
   (d) a second shell comprising a solid layer of silica, wherein the second shell is between the first shell and the surface of the nanoparticle or the second shell surrounds the first shell,
   wherein the photosensitizer is embedded in the mesoporous silica.

2. The photodynamic therapy system of claim 1, wherein the second shell is between the first shell and the surface of the nanoparticle.

3. The photodynamic therapy system of claim 2, wherein the second shell is from about 5 nm to about 1000 nm.

4. The photodynamic therapy system of claim 2, wherein the first shell is from about 5 nm to about 1000 nm.

5. The photodynamic therapy system of claim 1, wherein the nanoparticle is hydrolytic.

6. The photodynamic therapy system of claim 1, wherein the photosensitizer is cyanine, porphyrin, pyrrole, tetrapyrrollic compounds, expanded pyrrolic macrocycles, flavins, organometallic species, or combinations thereof.

7. The photodynamic therapy system of claim 1, wherein the photosensitizer is selected from the group consisting of merocyanine, phthalocyanine, chloroaluminum phthalocyanine, sulfonated aluminum phthalocyanine, ring-substituted cationic phthalocyanine, sulfonated aluminum naphthalocyanine, naphthalocyanine, tetracyanoethylene adduct, crystal violet, azure P chloride, benzophenothiazinium, benzophenothiazinium chloride (EtNBS), phenothiazine, rose Bengal, toluidine blue, toluidine blue O (TBO), methylene blue (MB), new methylene blue N (NMMB), new methylene blue BB, new methylene blue FR, 1,9-dimethylmethylene blue chloride (DMMB), methylene green, methylene violet Bernthsen, methylene violet 3RAX, Nile blue, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, and thionine.

8. The photodynamic therapy system of claim 1, wherein the photosensitizer is merocyanine 540.

9. The photodynamic therapy system of claim 1, wherein the electromagnetic radiation source produces radiation selected from the group consisting of X-rays, alpha particles, beta-particles, neutrons, gamma rays, and combinations thereof.

10. The photodynamic therapy system of claim 1, wherein the system further comprises a cell recognition moiety.

11. The photodynamic therapy system of claim 10, wherein the cell recognition moiety is selected from the group consisting of a receptor, ligand, polynucleotide, peptide, polynucleotide binding agent, antigen, antibody, or combinations thereof.

12. The photodynamic therapy system of claim 1, wherein the system further comprises a therapeutic agent.

13. A pharmaceutical composition, comprising:
    (a) the photodynamic therapy system according to claim 1; and
    (b) pharmaceutically acceptable excipient.

14. A method for photodynamic therapy in a subject, comprising:
    administering to the subject a photodynamic therapeutic system comprising a strontium aluminum oxide nanoparticle of formula $Sr_aAl_bO_c$, where a, b and c are integers from 1 to 30, doped with $Eu^{2+}$, $Dy^{3+}$, $Nd^{3+}$, or combinations thereof that emits electromagnetic radiation having a first wavelength when irradiated with electromagnetic radiation having a second wavelength and wherein nanoparticle is from 5 nm to 5000 nm, a photosensitizer which absorbs light of the first wavelength, and a first shell comprising a biocompatible mesoporous silica that forms a coating on the surface of the nanoparticle, a second shell comprising a solid layer of silica wherein the second shell is between the first shell and the surface of the nanoparticle or the second shell surrounds the first shell, wherein the photosensitizer is embedded in the mesoporous silica; and irradiating the system, thereby causing the nanoparticles to emit electromagnetic radiation having the first wavelength and the photosensitizer to absorb the electromagnetic radiation having the first wavelength.

* * * * *